United States Patent
Yamamura et al.

(12) 
(10) Patent No.: US 10,532,026 B2
(45) Date of Patent: Jan. 14, 2020

(54) THERMO-RESPONSIVE GELLING ARTIFICIAL LACRIMA

(71) Applicant: WAKAMOTO PHARMACEUTICAL CO., LTD., Tokyo (JP)

(72) Inventors: Takeshi Yamamura, Tokyo (JP); Ayaka Yamamuro, Tokyo (JP); Emi Izukura, Tokyo (JP); Moto Kimura, Tokyo (JP); Tomohiro Otsuka, Tokyo (JP)

(73) Assignee: WAKAMOTO PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/110,056

(22) Filed: Aug. 23, 2018

(65) Prior Publication Data

US 2018/0360746 A1 Dec. 20, 2018

Related U.S. Application Data

(63) Continuation of application No. PCT/JP2018/016854, filed on Apr. 25, 2018.

(30) Foreign Application Priority Data

Apr. 25, 2017 (JP) ................................. 2017-086512
Dec. 26, 2017 (JP) ................................. 2017-249891

(51) Int. Cl.
| | | |
|---|---|---|
| A61K 9/00 | (2006.01) | |
| A61P 27/02 | (2006.01) | |
| A61K 47/32 | (2006.01) | |
| A61K 47/10 | (2017.01) | |
| A61K 47/38 | (2006.01) | |
| A61K 9/06 | (2006.01) | |
| A61P 27/04 | (2006.01) | |
| A61K 31/194 | (2006.01) | |
| A61K 47/12 | (2006.01) | |
| A61K 31/5383 | (2006.01) | |

(52) U.S. Cl.
CPC .............. *A61K 9/0048* (2013.01); *A61K 9/06* (2013.01); *A61K 31/194* (2013.01); *A61K 31/5383* (2013.01); *A61K 47/10* (2013.01); *A61K 47/12* (2013.01); *A61K 47/32* (2013.01); *A61K 47/38* (2013.01); *A61P 27/02* (2018.01); *A61P 27/04* (2018.01)

(58) Field of Classification Search
CPC ........ A61K 9/0048; A61K 9/06; A61K 47/38; A61K 47/10; A61K 47/32; A61P 27/04; A61P 27/02

See application file for complete search history.

(56) References Cited

U.S. PATENT DOCUMENTS

| 5,591,426 A * | 1/1997 | Dabrowski .......... A61K 9/0048 424/78.04 |
|---|---|---|
| 2003/0194441 A1 | 10/2003 | Suzuki et al. |
| 2006/0172969 A1 | 8/2006 | Suzuki et al. |
| 2006/0211599 A1 | 9/2006 | Suzuki et al. |
| 2010/0197811 A1* | 8/2010 | Suzuki ................ A61K 9/0019 514/781 |
| 2011/0263587 A1 | 10/2011 | Suzuki |

FOREIGN PATENT DOCUMENTS

| JP | 2003-95924 A | 4/2003 |
|---|---|---|
| JP | 2003-342197 A | 12/2003 |
| JP | 2003342197 | * 12/2003 |
| JP | 2005343893 A | 12/2005 |
| JP | 2006176501 A | 7/2006 |
| WO | 02/11734 A1 | 2/2002 |
| WO | 2005/042026 A1 | 5/2005 |
| WO | 2009/001899 A1 | 12/2008 |

OTHER PUBLICATIONS

English translation of JP 2003/95924 (Year: 2003).*
The Japanese Pharmacopoeia, 17th Edition, Published by Tokyo Hirokawa Shoten, 2016, with translation of pertinent parts.
Lin, Chang-Ping et al., "Influences of Methylcellulose on Corneal Epithelial Wound Healing", Journal of Ocular Pharmacology and Therapeutics, vol. 15, No. 1, 1999, pp. 59-63.
Kobayashi, Shigeki. et al., "Effect of Ofloxacin gel forming ophthalmic solution 0.3% for superficial punctuate keratopathy (SPK) and corneal epithelial", Folia Japonica de Ophthalmologica Clinica 4 (2), 2011, pp. 132-137, with translation of pertinent parts.
Japanese Office Action dated Oct. 22, 2018, issued in JP Patent Application No. 2018-527825 with English translation attached.
"Handbook of pharmaceutical excipients"; New Edition; 2007; First Edition; pp. 825-831 and 838-845 with English translation attached.
Japanese Office Action dated Jul. 17, 2018, issued in JP Patent Application No. 2018-527825 with English translation attached.

* cited by examiner

*Primary Examiner* — Barbara P Badio
(74) *Attorney, Agent, or Firm* — Nath, Goldberg & Meyer; Joshua B. Goldberg

(57) ABSTRACT

The present invention is an aqueous solution which contains two types of methyl celluloses, polyethylene glycol, polyvinylpyrrolidone, and citric acid or a pharmaceutically acceptable salt thereof. The composition of the present invention maintains a low viscosity around room temperature, but the composition is suddenly increased in the viscosity due to heat around the body temperature and has thixotropy even after gelation.

2 Claims, 7 Drawing Sheets

THERMO-RESPONSIVE GELLING ARTIFICIAL LACRIMA

TECHNICAL FIELD

The present invention relates to an aqueous composition which increases viscosity around the human body temperature but the fluidity of which increases when a force is applied to the composition having increased viscosity. More particularly, the present invention relates to a thermo-responsive gelling artificial lacrima which contains methyl cellulose as a principal agent and which is used to treat dry eye and the like.

BACKGROUND ART

The lacrima is produced by the lacrimal gland located at an outer side of the eyelid, supplies moisture to the ocular surface, and is discharged from the lacrimal puncta, located in the inner corner of the eye, to the back of the nose. The lacrima form was said in the past to have a three-layer structure of the lipid layer, the aqueous layer, and the mucin layer on the ocular surface from the outer side to the cornea. In recent years, however, the concept which has become prevalent is that there is no partition between the aqueous layer and the mucin layer and mucins are mixed in the aqueous layer with a concentration gradient. Presently, the concept is that the ocular surface has a two-layer structure of the lipid layer and the aqueous layer having mucins mixed therein. Dry eye occurs if a problem arises in one of the two layers of this structure.

The "evaporative dry eye," which occurs when a problem arises in the lipid layer of the lacrima, includes meibomian gland dysfunction and blepharitis. The "aqueous deficient dry eye," which occurs when a problem arises in the aqueous layer of the lacrima, includes Sjögren's syndrome and the Stevens-Johnson syndrome.

In 2016, the Dry Eye Society defined that "Dry eye is a multifactorial disease of the tear film instability that results in symptoms of discomfort, visual disturbance and potential damage to the ocular surface."

The ultimate purpose of dry eye treatment is to restore the lacrima form to the normal and to ameliorate keratoconjunctival epithelial disorder and subjective symptom.

Instillations actually used for the treatment of dry eye include aqueous ophthalmic solutions, including an artificial lacrima, sodium hyaluronate, chondroitin sulfate sodium, and flavin adenine dinucleotide, serum instillations, oil instillation, and the like. In recent years, therapeutic agents for dry eyes such as diquafosol sodium and rebamipide are commercially available. In the case of a mild degree of dry eye, OTC ophthalmic drugs as an artificial lacrima having an efficacy and effect of supplying the lacrima (drying of eye) are easily available in Japan.

The role of an artificial lacrima is a method of increasing the lacrima by supplying deficient lacrima from the outside. The amount of lacrima has reported to be 6.5±0.3 µL for an ordinary person and 4.8±0.4 µL for a dry eye patient, the capacity of the conjunctival sac is 20 to 30 µL, and one drop of ophthalmic solution is about 50 µL. Thus, if one drop of artificial lacrima is instilled to one eye, the conjunctival sac is filled with water in the cases of both an ordinary person and a dry eye patient.

An artificial lacrima is, for example, an aqueous ophthalmic solution added with inorganic salts. However, after instillation, a phenomenon takes place in which such an aqueous ophthalmic solution is rapidly discharged through the nasolacrimal duct or evaporates from the ocular surface. Thus, for the purpose of maintaining moisture on the ocular surface or mitigating subjective symptoms, frequent instillation is required, for example 2 or 3 drops at a time and 5 or 6 times per day (Non Patent Literatures 1 to 3).

Ophthalmic solutions are commercially available which are blended with a water soluble polymer to obtain a high viscosity for the purpose of delaying such discharge of an artificial lacrima from the ocular surface and further supplying a large amount of water. As the water soluble polymer, for example, hypromellose (HPMC), hydroxyethyl cellulose (HEC), or hyaluronic acid and a pharmaceutically acceptable salt thereof are added as a thickening agent. However, it is known that such an ophthalmic solution is high in viscosity and thus it is difficult to adjust the amount added dropwise at the time of application and that discomfort such as blurred vision after instillation is caused.

It is known that among the water soluble polymers, methyl cellulose being a cellulose derivative is a cornea surface layer protection agent, and 0.5% methyl cellulose-containing physiological saline provides water retainability to the surface of the cornea, forming a thin film having properties similar to those of the lacrima (Non Patent Literature 4).

In addition, it is known that 0.6% and 1.2% methyl cellulose-containing physiological salines provided a therapeutic effect for a wound in the corneal epithelium of a pig eyeball (Non Patent Literature 5).

However, in these methyl cellulose-containing physiological salines, the property of forming into gel due to heat, which is specific to methyl cellulose, was not observed on the solution. The effects by gelation are not considered at all.

As an aqueous pharmaceutical composition containing methyl cellulose, it is described that a thermo-responsive gelling formulation which contains methyl cellulose, and hyaluronic acid and pharmaceutically acceptable salts thereof or a thermo-responsive gelling artificial lacrima which contains methyl cellulose, MACROGOL 4000, and sodium citrate is used for the purpose of increasing the amount of lacrima by gelation around the body temperature, supplying water to the ocular surface, and protecting the lipid layer of the lacrima (Patent Literatures 1 and 2).

On the other hand, a thermo-responsive gelling aqueous pharmaceutical composition is disclosed which contains a new quinolone-based antibacterial agent as an active ingredient and which has a sufficiently low gelling temperature. In addition, as the composition mentioned above, an ofloxacin gel forming ophthalmic solution 0.3% "WAKAMOTO" is reported to have an effect for conical epithelial disorders (Patent Literature 3 and Non Patent Literature 6).

The foregoing only describes an effect of a gel forming ophthalmic solution containing one type of methyl cellulose in a gel forming ophthalmic solution containing an antibacterial agent. The above aqueous pharmaceutical compositions disclosed in these Patent Literatures are usually assumed to be stored at low temperatures because, if stored at room temperature, the composition gradually forms into gel and a characteristic of being easily applied in the form of liquid before instillation is lost. Although frequent instillation is generally carried out in the case of an artificial lacrima as described above, the reversible thermo-responsive gelling aqueous composition is inappropriate to carry with because it needs to be stored at low temperatures.

As an aqueous pharmaceutical composition containing any of methyl cellulose, polyethylene glycol, and sodium citrate, sugar alcohol, lactose, carmellose, and cyclodextrin, disclosed is a composition which, even if formed into gel at room temperature, rapidly decreases in viscosity and transforms back to liquid when a weak force is applied thereto, such as when the aqueous pharmaceutical composition is shook gently. In other words, an aqueous composition having thixotropy is disclosed (Patent Literature 4).

Regarding an aqueous composition which is made up of an aqueous solution containing hydroxyethyl cellulose, methyl cellulose, or hypromellose, disclosed is a composition which does not rapidly increase viscosity around the human body temperature to form a gel but rapidly decreases in viscosity and increases in fluidity when a weak force is applied such as when the aqueous composition is shook gently (Patent Literature 5).

As described above, with focus on distribution of products and on QOL, improvements have been carried out, including portable thermo-responsive gelling formulations and aqueous compositions which do not produce a feeling of foreign matter after application. However, an aqueous composition which achieves thixotropy by repetition of sol-gel phase transitions is not disclosed.

As described above, an aqueous composition made by combining methyl celluloses with different standards at a particular ratio is not known at all which forms into gel around the body temperature but transitions to sol when a physical stimulus is applied and which exhibits reproducibility.

In addition, an aqueous composition made by combining methyl celluloses with different specifications at a particular ratio is not known at all which has a function to protect the cornea or a function to mitigate corneal epithelium disorders by forming into gel around the body temperature.

CITATION LIST

Patent Literatures

Patent Literature 1: Japanese Patent Application Publication No. 2003-342197
Patent Literature 2: Japanese Patent Application Publication No. 2003-95924
Patent Literature 3: WO 02/011734
Patent Literature 4: WO 2005/042026
Patent Literature 5: WO 2009/001899

Non Patent Literatures

Non Patent Literature 1: Ganka Care (The Japanese Journal of Ophthalmic Caring), extra issue in 2010 winter (148th issue), MEDICUS SHUPPAN, Publishers Co., Ltd., Shigeru KINOSHITA and editors, 145-147
Non Patent Literature 2: Diagnosis and Treatment of Ocular Surface-Dry Eye-, Medical-Aoi Publications, Inc, supervised by Yoshihisa OGUCHI
Non Patent Literature 3: Web site of the Dry Eye Society (www.dryeye.ne.jp/)
Non Patent Literature 4: The Japanese Pharmacopoeia, 17th Edition, Published by Tokyo Hirokawa Shoten
Non Patent Literature 5: Journal of Ocular Pharmacology and Therapeutics, Volume 15, Number 1, 1999, 59-63
Non Patent Literature 6: Folia Japonica de Ophthalmologica Clinica 4 (2), 2011, 132-137

SUMMARY OF INVENTION

Technical Problems

A problem to be solved by the present invention is to provide an ophthalmic aqueous composition in which a low viscosity is maintained around room temperature (for example, around 25° C.) but the viscosity suddenly increases due to heat around the body temperature, making it possible to retain lacrima on the ocular surface.

Another problem to be solved by the present invention is to provide an ophthalmic aqueous composition for protecting the cornea, for mitigating corneal epithelial disorders, or for recovery from corneal damage.

Yet another problem to be solved by the present invention is to provide use of methyl cellulose for preparing an ophthalmic aqueous composition for protecting the cornea, for mitigating corneal epithelial disorders, or for recovery from corneal damage.

Solution to Problems

The present invention is an aqueous solution including methyl celluloses, polyethylene glycol, polyvinylpyrrolidone, and citric acid or a pharmaceutically acceptable salt thereof which has been completed based on our finding that the problems described above can be solved by combining two or more types of methyl celluloses different in a specification (for example, viscosity). To be more specific, the present invention provides ophthalmic aqueous compositions; an ophthalmic aqueous composition for protecting the cornea, mitigating conical epithelial disorders, or recovery from conical damage; and use of methyl celluloses for preparing an ophthalmic aqueous composition for protecting the cornea, mitigating corneal epithelial disorders, or recovery from conical damage below.

1. An ophthalmic aqueous composition comprising: (A) at least two types of methyl celluloses; (B) polyethylene glycol; (C) polyvinylpyrrolidone; and (D) citric acid or a pharmaceutically acceptable salt thereof, wherein the ophthalmic aqueous composition has a gelling property.
2. The ophthalmic aqueous composition according to 1 described above, wherein the (A) component comprises two types of methyl celluloses.
3. The ophthalmic aqueous composition according to 2 described above, wherein the two types of methyl celluloses are contained at a mass ratio of 1:30 to 30:1.
4. The ophthalmic aqueous composition according to any one of 1 to 3 described above, wherein the (A) component is methyl cellulose having a viscosity of 2-w/v %-aqueous solution at 20° C. being 4 to 400 mPa·s.
5. The ophthalmic aqueous composition according to any one of 1 to 3 described above, wherein the (A) component comprises two members selected from the group consisting of methyl celluloses having viscosities of 2-w/v %-aqueous solution at 20° C. being 4 mPa·s, 15 mPa·s, 25 mPa·s, 100 mPa·s, 400 mPa·s, 1500 mPa·s, and 4000 mPa·s.
6. The ophthalmic aqueous composition according to any one of 1 to 5 described above, wherein the (B) component is at least one selected from the group consisting of PEG 8000, PEG 4000, PEG 800, PEG 400, and PEG 300.
7. The ophthalmic aqueous composition according to any one of 1 to 6 described above, wherein the (C) component is at least one selected from the group consisting of PVP K17, PVP K25, PVP K30, and PVP K90.
8. The ophthalmic aqueous composition according to any one of 1 to 7 described above, which is a thermo-responsive gelling artificial lacrima.
9. An ophthalmic aqueous composition for protecting cornea, mitigating a corneal epithelium disorder, or recovery from a conical disorder, comprising: (A) at least two types of methyl celluloses; (B) polyethylene glycol; (C) polyvinylpyrrolidone; and (D) citric acid or a pharmaceutically acceptable salt thereof.

10. Use of at least two types of methyl celluloses in combination with polyethylene glycol, polyvinylpyrrolidone, and citric acid or a pharmaceutically acceptable salt thereof for preparing an ophthalmic aqueous composition for protecting cornea, mitigating a corneal epithelial disorder, or recovery from a corneal disorder.

Advantageous Effects of Invention

An ophthalmic aqueous composition of the present invention can be used as a therapeutic drug for corneal epithelial disorders such as dry eye or as an artificial lacrima for supplying lacrima. In that case, it is used as an ophthalmic solution applied to the eyes of mammals, especially humans. When administered to an organism such as a human, this composition easily increases viscosity at the body temperature thereof. In addition, although the composition of the present invention increases viscosity in an environment with a high temperature in a certain region, season, and the like, the composition can be easily administered to an organism because, thanks to thixotropy, the composition, when shaken and mixed gently, comes to have high fluidity (in other words, changes into a sol) and accordingly can repeat sol-gel phase transition.

Figure 1:
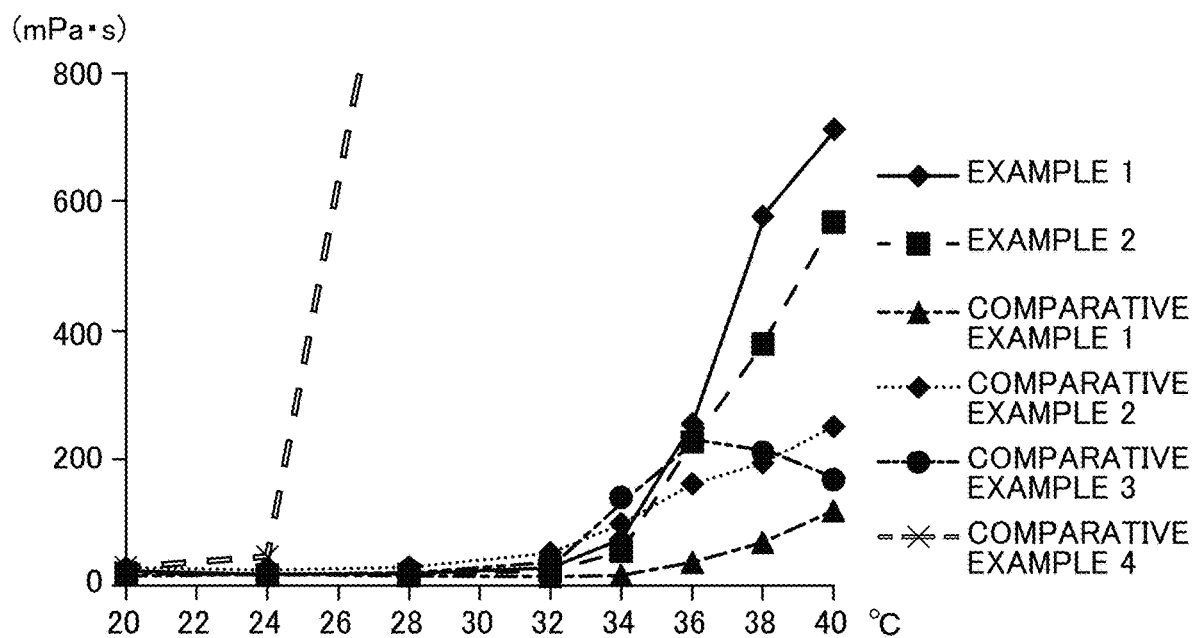
FIG. 1 shows gelling temperatures in Examples and Comparative Examples of the present invention.

DESCRIPTION OF EMBODIMENTS (A) At Least Two Types of Methyl Celluloses

As the methyl cellulose (hereinafter also referred to as MC) used in the present invention, ones commercially available as pharmaceutical additives can appropriately be used. In terms of viscosity, for example, the viscosity of 2-w/v %-aqueous solution at 20° C. may be 12000 mPa·s (millipascal-seconds) or less and more preferably 120 mPa·s or less. The content of methoxy group is preferably within a range of 26 to 33%. Furthermore, MC is classified depending on the viscosity of the aqueous solution. For example, the varieties of commercial products include ones having label viscosities of 4, 15, 25, 100, 400, 1500, and 4000, which are easily available (the numbers indicate the viscosity of a 2-w/v %-aqueous solution at 20° C. (the unit is millipascal-seconds). Hereinafter, the same applies to the case of simply referring to "viscosity" or "label viscosity." For example, "label viscosity is 4" means that the viscosity of a 2-w/v %-aqueous solution at 20° C. is 4 millipascal-seconds.). MC having a label viscosity of 4 to 400 is preferable because of easiness to handle, more preferably two types of MCs selected from the group consisting of MCs with label viscosities of 4, 15, 25, 100, 400, 1500, and 4000, further preferably MC having a label viscosity of 4, MC having a label viscosity of 15, and MC having a label viscosity of 400, particularly preferably a combination of MC having a label viscosity of 4 and MC having a label viscosity of 15, a combination of MC having a label viscosity of 4 and MC having a label viscosity of 400, and a combination of MC having a label viscosity of 15 and MC having a label viscosity of 400, and especially preferably a combination of MC having a label viscosity of 4 and MC having a label viscosity of 15. The Encyclopedia of Pharmaceutical Additives (edited by the International Pharmaceutical Excipients Council Japan and published by Yakuji Nippo, Limited) describes the details of the overview, specifications, applications, amount used, trade names, and the like of MC. In addition, MC is described in the Japanese Pharmacopoeia, 17th Edition, as an article of pharmaceutical drug specified based on investigation and agreement in three pharmacopoeias of Japan, the United States, and Europe. Most of the specifications of MC are common in the three pharmacopoeias. Note that the viscosity of MC can be measured in accordance with the method described in the Japanese Pharmacopoeia, 17th Edition.

(B) Polyethylene Glycol

The polyethylene glycol (hereinafter also referred to as PEG) used in the present invention is commercially available as a pharmaceutical additive and is marketed by, for example, Wako Pure Chemical Industries, Ltd. under the trade names of PEG-200, -300, -400, -600, -1000, -1500, -1540, -2000, -4000, -6000, -8000, -20000, -50000, -500000, -2000000, and -4000000, by Sanyo Chemical Industries, Ltd. under the trade names of MACROGOL-200, -400, -1500, -4000, -6000, or -20000, and by DOW CHEMICAL COMPANY under the trade names of CARBOWAX (registered trademark) PEG 200, 300, 400, 540, 600, 1000, 1450, 3350, 4000, 4600, and 8000. The weight average molecular weight of the PEG used as the base of the present invention is preferably 300 to 50000 and particularly preferably 300 to 8000. The preferableness is because if the weight average molecular weight is 300 or more, the sol-gel phase transition by body temperature is likely to occur, and if the weight average molecular weight is 50000 or less, the viscosity in the liquid state is not too high. In particular, PEG having a weight average molecular weight of 4000 or 8000 is preferable. In addition, it is also possible to adjust the weight average molecular weight within the above appropriate range by mixing two or more types of PEGs. The Encyclopedia of Pharmaceutical Additives (edited by the International Pharmaceutical Excipients Council Japan and published by Yakuji Nippo, Limited) describes the details of the overview, specifications, applications, amount used, trade names, and the like of PEG. In addition, an overview and the specifications of PEG are described in detail in the United States Pharmacopeia (2018 U.S. Pharmacopeia National Formulary, USP41 NF36, hereinafter referred to as USP41 (NF36)). Note that the weight average molecular weights of PEG-400, -4000, -6000, and -20000 can be measured in accordance with the method described in the Japanese Pharmacopoeia, 17th Edition. It is possible to measure the viscosity of PEG having a weight average molecular weight of 200 to 8000 in accordance with USP41 (NF36), and the viscosity ranges of these types of PEG are specified in USP41 (NF36).

Polypropylene Glycol

Instead of PEG or in addition to PEG, it is possible to use polypropylene glycol. If polypropylene glycol is contained, it is possible to adjust the viscosity of the composition of the present invention to an appropriate range. Polypropylene glycol applicable to the present invention has a weight average molecular weight of preferably 200 to 40000, more preferably 200 to 1200, further preferably 200 to 700 due to a high solubility to water, and particularly preferably 200 to 400. Note that the weight average molecular weight of polypropylene glycol 2000 can be measured in accordance with the method described in Japanese Pharmaceutical Excipients 2013 (published by Yakuji Nippo, Limited). Polypropylene glycol is marketed by, for example, NOF Corporation under the trade name of UNIOL (registered trademark) D-200, D-250, D-400, D-700, D-1000, D-1200, D-2000, and D-4000. The weight average molecular weight and the kinematic viscosity of the above-described UNIOL D series are described in Oleo & Speciality Chemicals Product Comprehensive Catalogue (Oleo & Speciality Chemicals Division of NOF Corporation).

(C) Polyvinylpyrrolidone

As the polyvinylpyrrolidone (hereinafter also referred to as PVP) used in the present invention, ones commercially available as pharmaceutical additives can appropriately be used. Specifically, examples include PVP K17, PVP K25, PVP K30, PVP K90, and the like. The weight average molecular weight of the PVP used in the present invention is preferably 2500 to 250000 and particularly preferably 20000 to 150000. PVP is preferably at least one selected from the group consisting of PVP K17, PVP K25, PVP K30, and PVP K90, and especially preferably PVP K25. The Encyclopedia of Pharmaceutical Additives (edited by the International Pharmaceutical Excipients Council Japan and published by Yakuji Nippo, Limited) describes the details of the overview, specifications, applications, amount used, trade names, and the like of PVP. PVP K25, PVP K30, and PVP K90 are listed as a povidone in the Japanese Pharmacopoeia, 17th Edition. Povidone is described in the Japanese Pharmacopoeia, 17th Edition, as an article of pharmaceutical drug specified based on investigation and agreement in three pharmacopoeias of Japan, the United States, and Europe. Most of the specifications of povidone are common in the three pharmacopoeias. Note that PVP K25 may be written as PVP k25 in the present invention.

(D) Citric Acid or Pharmaceutically Acceptable Salt Thereof

The citric acid used in the present invention includes citric acid hydrate and a pharmaceutically acceptable salt of citric acid.

As the examples of the pharmaceutically acceptable salt of citric acid described above, it is possible to list a sodium salt, a potassium salt, and the like. The sodium salt includes sodium citrate hydrate (another name: sodium citrate (Japanese Pharmacopoeia), hereinafter referred to as sodium citrate), sodium dihydrogen citrate, disodium citrate, and the like. The potassium salt includes potassium citrate (potassium citrate monohydrate).

Sodium citrate used in the present invention is described in detail in the Japanese Pharmacopoeia, 17th Edition, including an overview, specifications, and usage as sodium citrate hydrate. In addition, USP41 (NF36) describes the details of the overview and the specifications of sodium citrate dihydrate as sodium citrate.

The MC in the ophthalmic aqueous composition of the present invention has the total concentration of preferably 0.2 to 5 w/v %. The composition of the present invention preferably has a total concentration of the MC being 0.2 w/v % or more because the composition having such total concentration of the MC easily gelates at the temperature of the ocular surface. In addition, a total concentration of the MC being 5 w/v % or less is preferable because the viscosity can be adjusted within an easy-to-handle range. The concentration is more preferably 0.5 w/v % or more and further preferably 1 w/v % or more. Additionally, the concentration is more preferably 4 w/v % or less and further preferably 3 w/v % or less.

As an embodiment of the ophthalmic composition of the present invention, it is possible to blend three or more types of MCs different in the standard. A composition made by blending three or more types of MCs is preferable because it increases viscosity relatively rapidly at around the human body temperature (34 to 38° C.) compared to a composition of one type of MC. A composition made by blending two types of MC is further preferable because it is easy to adjust the viscosity so that the composition can be stored in the form of liquid (sol) at room temperature (1 to 30° C.).

If two types of MCs are used in combination, the concentration of one type of MC in the above composition is preferably 0.1 to 3 w/v %. A concentration of the MC being 0.1 w/v % or more is preferable because it increases viscosity around the human body temperatures (34 to 38° C.). In addition, a concentration of the MC being 3 w/v % or less is preferable because it is easy to prepare an aqueous solution having a low viscosity at room temperature (1 to 30° C.). The concentration is more preferably 0.1 w/v % or more and further preferably 0.2 w/v % or more. The concentration is more preferably 2.5 w/v or more.

If two types of MCs are used in combination, the MCs different in the specification (preferably, viscosity) are mixed in a mass ratio of preferably 1:30 to 30:1, more preferably 1:24 to 24:1, and further preferably 1:4 to 4:1. In particular, it is preferable to use a combination of MC having a label viscosity of 4 and MC having a label viscosity of 15, a combination of MC having a label viscosity of 4 and MC having a label viscosity of 400, and a combination of MC having a label viscosity of 15 and MC having a label viscosity of 400 in the above mass ratio. It is especially preferable to use a combination of MC having a label viscosity of 4 and MC having a label viscosity of 15 in the above mass ratio, and in that case, it is preferable to use in a mass ratio of 1:4 to 4:1.

As an embodiment of the ophthalmic aqueous composition of the present invention, the components other than the MC preferably have the following concentration ranges.

The concentration of PEG is within the range of 0.5 to 4.0 w/v %. A range outside the above is not preferable. If the concentration is lower than 0.5 w/v %, local production of gel is unlikely to take place, hence resulting in insufficient practical use. In addition, if the concentration is higher than 4 w/v %, the gelling temperature becomes low.

The concentration of polypropylene glycol is within the range of 0.1 to 4 w/v %, and the concentration higher than 4 w/v % is not preferable because of eye stimulus.

The concentration of PVP is within the range of 0.5 to 4.0 w/v %. A range outside the above is not preferable. If the concentration is lower than 0.5 w/v %, local production of gel is unlikely to take place, hence resulting in insufficient practical use. In addition, if the concentration is higher than 4 w/v %, the viscosity of sol becomes high.

The concentration of citric acid is within the range of 1.0 to 4.0 w/v %. If the concentration is lower than 1.0 w/v %, local production of gel is unlikely to take place, hence resulting in insufficient practical use. In addition, a concentration higher than 4 w/v % is not preferable in terms of eye stimulus.

The composition of the present invention most preferably contains:
(A) MC having a label viscosity of 4 and MC having a label viscosity of 15 in such an amount that a mass ratio is 1:4 to 4:1 and a total concentration is 0.2 to 5 w/v %;
(B) PEG having a weight average molecular weight of 4000 or 8000 at 0.5 to 4.0 w/v %;
(C) PVP K25 at 0.5 to 4.0 w/v %; and
(D) citric acid or sodium salts thereof at 1.0 to 4.0 w/v %.
The pH adjuster of this composition may be sodium hydroxide or sulfuric acid.

The ophthalmic aqueous composition of the present invention is desired to gelate at temperatures around the mammal body temperature. For this reason, the gelling temperature (the temperature at which phase transition from sol to gel takes place) of the ophthalmic aqueous composition of the present invention is preferably about 30° C. to 40° C. and more preferably 34° C. to 40° C. The ophthalmic aqueous composition of the present invention can be stored at room temperature (1 to 30° C). as a liquid which can be readily administered at room temperature. By adjusting the concentrations of the components (B) to (D) described above, it is possible to finely adjust the gelation temperature.

The ophthalmic composition of the present invention can be used as a therapeutic drug for corneal epithelial disorders such as dry eye.

The ophthalmic aqueous composition of the present invention can also be used as an artificial lacrima for supplying lacrima in the case of keratoconjunctivitis sicca and lacrimal hyposecretion, an artificial lacrima for supplying lacrima in the case of discomfort, drying of the eye, eye strain, and blurred vision when wearing contact lenses attributed to insufficient lacrima, and an artificial lacrima for supplying lacrima in the case of sore symptom and stimulus attributed to drying of the eye.

The ophthalmic aqueous composition of the present invention can also be used as an artificial lacrima which protects the cornea by suppressing drying of the cornea or an artificial lacrima which increases the amount of lacrima.

The ophthalmic aqueous composition of the present invention can also be used as an artificial lacrima which retains on the ocular surface and mitigates corneal epithelium disorders.

The ophthalmic aqueous composition of the present invention can also be used as an artificial lacrima which can heal corneal disorders by recovering early from conical damage.

As active ingredients for dry eye or active ingredients for artificial lacrima, the ophthalmic aqueous composition of the present invention may be blended with inorganic salts such as sodium chloride, potassium chloride, calcium chloride, sodium hydrogen carbonate, sodium carbonate, dried sodium carbonate, magnesium sulfate, sodium hydrogenphosphate, disodium hydrogenphosphate, and potassium dihydrogen phosphate, saccharides such as glucose, amino acids such as potassium L-aspartate, magnesium L-aspartate, magnesium. potassium L-aspartate [equal amount mixture], aminoethylsulfonic acid (hereinafter also referred to as taurine), and chondroitin sulfate sodium or pharmaceutically acceptable salts thereof, and polymer compounds such as polyvinyl alcohol, hyaluronic acid and pharmaceutically acceptable salts thereof, hydroxyethyl cellulose, and hypromellose (hydroxypropyl methyl cellulose). The amount of these active ingredients blended is not particularly limited as long as the concentration is such that the expected efficacy can be obtained.

The ophthalmic aqueous composition of the present invention is usually adjusted to a pH of 3 to 10 and is adjusted in particular to a pH of preferably 5 to 8 in terms of eye stimulus. Various types of pH adjusters usually added may be used in order to adjust the pH of the artificial lacrima of the present invention. Examples include acids, bases, amino acids, and the like. The acids include, for example, hydrochloric acid, sulfuric acid, phosphoric acid, boric acid, acetic acid, lactic acid, gluconic acid, ascorbic acid, and the like. The bases include, for example, potassium hydroxide, calcium hydroxide, sodium hydroxide, magnesium hydroxide, monoethanolamine, diethanolamine, triethanolamine, and the like. The amino acids include glycine, histidine, epsilon-aminocaproic acid, and the like.

The ophthalmic aqueous composition of the present invention may contain a pharmaceutically acceptable isotonic agent, solubilizing agent, preservative, antiseptic, and the like as necessary. The isotonic agent includes saccharides such as xylitol, mannitol, and glucose, propylene glycol, glycerin, sodium chloride, potassium chloride, and the like. The solubilizing agent includes Polysorbate 80, polyoxyethylene-hardened castor oil, and cyclodextrin.

The preservative usable includes ionic preservatives such as benzalkonium chloride (hereinafter also referred to as BAC), benzethonium chloride, and cetylpyridinium chloride, biguanide-based preservatives such as chlorhexidine gluconate, chlorhexidine hydrochloride, 1,1-dimethylbiguanide hydrochloride, polyhexamethylene biguanide, alexidine, hexetidine, and N-alkyl-2-pyrrolidinone, polyquaternium-based preservatives such as polidronium chloride, parabens such as methyl parahydroxybenzoate, propyl parahydroxybenzoate, butyl parahydroxybenzoate, alcohols such as chlorobutanol, phenylethyl alcohol, bronopol, and benzyl alcohol, organic acids and salts thereof such as sodium dehydroacetate, sorbic acid, and potassium sorbate.

Benzalkonium chloride, which is often used for an ophthalmic solution as an antiseptic agent, is represented by the general formula: [C6H5CH2N(CH3)2R]Cl. Note that in the general formula, R represents an alkyl group. In the composition of the present invention, benzalkonium chloride used was one marketed by Okami Chemical Industry Co., Ltd.

In addition, other additives include thickeners such as hydroxyethyl cellulose, polyvinyl alcohol, propylene glycol, diethylene glycol, hyaluronic acid and pharmaceutically acceptable salts thereof, chondroitin sulfate sodium and sodium polyacrylate, and stabilizers such as EDTA (ethylenediaminetetraacetate) and pharmaceutically acceptable salts thereof, tocopherols and derivatives thereof, and sodium sulfite.

A method of producing the ophthalmic aqueous composition of the present invention is not particularly limited and for example includes dispersing methyl cellulose, polyethylene glycol, polyvinylpyrrolidone, and citric acid into hot water of about 60 to 70° C. followed by cooling to 10° C. or below. Here, as necessary, inorganic salts, other active ingredients, additives, and the like are added and dissolved, followed by sufficient mixing. The pH of the obtained solution is adjusted with a pH adjuster as necessary, and sterile purified water is supplied to obtain a desired volume. Thus, the ophthalmic aqueous composition of the present invention is prepared. After the sterilization, the composition is filled into a plastic instillation bottle for use. The ophthalmic aqueous composition of the present invention is used as an ophthalmic solution applied to the eyes of mammals, especially humans.

Hereinafter, a detailed description is further provided for the present invention with reference to Examples. However, the present invention is not limited only to these Examples.

TEST EXAMPLE 1A

Methyl cellulose (manufactured by Shin-Etsu Chemical Co., Ltd., METOLOSE (registered trademark) SM-4 and SM-15), polyethylene glycol (CARBOWAX (registered trademark) PEG 8000, manufactured by DOW CHEMICAL COMPANY), polyvinylpyrrolidone (PVP k25), and sodium citrate were mixed in predetermined amounts, added to sterile purified water heated to 60 to 70° C., and dispersed by stirring. After uniform dispersion was confirmed, the mixture was cooled to 10° C. or below while being stirred. After it was confirmed that the entirety turned transparent, a predetermined amount of benzalkonium chloride was added, followed by dissolution. Moreover, the pH was adjusted to 7.0 with a 1 M aqueous solution of sodium hydroxide or a 1 M aqueous solution of sulfuric acid. After that, sterile purified water was supplied to obtain a predetermined volume. Thus, the ophthalmic aqueous composition of the present invention was prepared (Examples 1 and 2). Table 1 shows the formulation content.

Note that the amount of each component blended is represented in w/v %.

TABLE 1

| (w/v %) | Example 1 | Example 2 |
|---|---|---|
| Methyl Cellulose (SM-4) | 1.3 | 1.3 |
| Methyl Cellulose (SM-15) | 1.2 | 1.2 |
| Sodium Citrate Hydrate | 2.2 | 2.2 |
| PVP k25 | 2.5 | 2.0 |
| Polyethylene Glycol 8000 | 2.0 | 2.0 |
| Benzalkonium Chloride | 0.005 | 0.005 |
| pH Adjuster | q.s. | q.s. |
| pH | 7.0 | 7.0 |

As Comparative Examples, Examples-3 and -4 of Patent Literature 1, Example-7 of Patent Literature 4, and Example-5 of Patent Literature 3 were prepared in accordance with the methods described in the corresponding Patent Literatures (Comparative Examples 1 to 4). Table 2 shows the formulation content.

TABLE 2

| (w/v %) | Comp. Ex. 1 Patent Literature 1, Ex.-3 | Comp. Ex. 2 Patent Literature 1, Ex. 4 | Comp. Ex. 3 Patent Literature 4, Ex.-7 | Comp. Ex. 4 Patent Literature 3, Ex. 5 |
|---|---|---|---|---|
| Methyl Cellulose (SM-4) | 3.0 | 2.0 | 1.2 | 4.0 |
| Hyaluronic Acid Na | 0.1 | 0.1 | — | — |
| Sodium Citrate | 2.0 | 3.53 | 3.5 | 3.5 |
| Polyethylene Glycol 4000 | — | 2.0 | 2.0 | 4.0 |
| β-Cyclodextrin | — | — | 0.8 | — |
| Benzalkonium Chloride | 0.005 | 0.005 | — | — |
| Ofloxacin | — | — | — | 0.3 |
| pH Adjuster | q.s. | q.s. | q.s. | q.s. |
| pH | 6.5 | 6.5 | 7.0 | 6.5 |

The viscosity behavior of each aqueous composition was observed in order to investigate the relationship between temperature and viscosity for Examples or Comparative Examples shown in Tables 1 and 2.

The relationship between temperature and viscosity was evaluated by measuring the viscosities at 20° C. to 40° C. of the compositions of Examples 1 and 2 and Comparative Examples 1 to 4. The viscosity was measured with a rheometer manufactured by Anton-Paar (Modular Compact Rheometer 102). About 1 mL of the prepared composition of the present invention was set between a parallel plate having a diameter of about 50 mm and a temperature control peltier. The gap between the peltier and the parallel plate was set to 0.5 mm. Before the start of measurement, the sample was kept cool at 5° C. for 5 minutes. The temperature was caused to gradually rise to the measurement temperature from the start of measurement. The viscosity was measured while retaining the sample at the measurement temperature for 240 seconds. FIG. 1 shows the results.

Examples 1 and 2 being the compositions of the present invention maintained a low viscosity until 32° C., and the viscosity suddenly increased between 34° C. and 40° C. In Comparative Example 1, although the viscosity increased to some extent between 34° C. and 40° C., the viscosity was at a low level as a whole. In Comparative Examples 2 and 3, the viscosity increased from 32° C., and in Comparative Example 4, the viscosity suddenly increased at around 25° C.

In Comparative Examples 2 and 3, the gelling temperature is closer to room temperature than that of the composition of the present invention is, and Comparative Example 4 increases viscosity to a great extent at room temperature. Thus, it has been shown that storage at room temperature is difficult. On the other hand, it has been shown that the ophthalmic aqueous composition of the present invention can be stored as a liquid which can be readily administered at room temperature (1 to 30° C.).

TEST EXAMPLE 1B

Examples 4 to 39 were prepared in the same manner as Examples 1 and 2 described above as follows. Methyl cellulose (SM-4, SM-15, and SM-400), polyethylene glycol (PEG 8000, PEG 4000, PEG 400, and PEG 300), polyvinylpyrrolidone (PVP k25, PVP k30, and PVP k90), and sodium citrate were mixed in predetermined amounts, followed by further mixture with a predetermined amount of boric acid or hyaluronic acid in the case of preparing Examples in Table 6, added to sterile purified water heated to 60 to 70° C., and dispersed by stirring. After uniform dispersion was confirmed, the mixture was cooled to 10° C. or below while being stirred. After it was confirmed that the entirety turned transparent, a predetermined amount of other components shown in Tables 3 to 7 was added, followed by dissolution. Moreover, the pH was adjusted with a 1 M aqueous solution of sodium hydroxide or a 1 M aqueous solution of sulfuric acid. After that, sterile purified water was supplied to obtain a predetermined volume. Thus, the ophthalmic aqueous composition of the present invention was prepared.

Comparative Example A was prepared in the same procedures as those of Examples.

Tables 3 to 7 show the formulation content.

The relationship between temperature and viscosity was evaluated by measuring the viscosities at 20° C. to 40° C. of the compositions of Examples 4 to 39 and Comparative Example A. The viscosity was measured with a rheometer manufactured by Anton-Paar (Modular Compact Rheometer 102). About 1 mL of the prepared composition of the present invention was set between a parallel plate having a diameter of about 50 mm and a temperature control peltier. The gap between the peltier and the parallel plate was set to 0.5 mm. Before the start of measurement, the sample was kept cool at 5° C. for 5 minutes. The temperature was caused to gradually rise to the measurement temperature from the start of measurement. The viscosity was measured while retaining the sample at the measurement temperature for 240 seconds. Tables 3 to 7 show the results.

TABLE 3

| (w/v %) | | Ex. 4 | Ex. 5 | Ex. 6 | Ex. 7 | Ex. 8 | Ex. 9 | Ex. 10 | Comp. Ex. A |
|---|---|---|---|---|---|---|---|---|---|
| Methyl Cellulose (SM-4) | | 1.0 | 1.2 | 1.25 | 1.5 | 2.4 | — | — | — |
| Methyl Cellulose (SM-15) | | 1.5 | 1.3 | 1.25 | 1.0 | 0.1 | 2.4 | 2.0 | — |
| Methyl Cellulose (SM-400) | | — | — | — | — | — | 0.1 | 0.5 | 2.5 |
| Sodium Citrate Hydrate | | 2.2 | 2.2 | 2.2 | 2.2 | 2.2 | 2.2 | 2.2 | 2.2 |
| PVP k25 | | 2.0 | 2.0 | 2.0 | 2.0 | 2.0 | 2.0 | 2.0 | 2.0 |
| Benzalkonium Chloride | | 0.005 | 0.005 | 0.005 | 0.005 | 0.005 | 0.005 | 0.005 | 0.005 |
| Polyethylene Glycol 8000 | | 2.0 | 2.0 | 2.0 | 2.0 | 2.0 | 2.0 | 2.0 | 2.0 |
| pH Adjuster | | q.s. | q.s. | q.s. | q.s. | q.s. | q.s. | q.s. | q.s. |
| pH | | 7.0 | 7.0 | 7.0 | 7.0 | 7.0 | 7.0 | 7.0 | 7.0 |
| Viscosity (mPa · s) | 20° C. | 38.6 | 22.5 | 22.8 | 20.2 | 11.6 | 78.2 | 99.1 | 1260 |
| | 24° C. | 32.0 | 19.6 | 19.8 | 17.7 | 9.94 | 63.8 | 80.7 | 1040 |
| | 28° C. | 30.9 | 17.4 | 17.9 | 16.1 | 8.9 | 66.1 | 69.6 | 916 |
| | 32° C. | 56.0 | 20.5 | 22.1 | 22.1 | 9.8 | 119 | 103 | 2000 |
| | 34° C. | 176 | 62.1 | 76.4 | 90.1 | 24.8 | 258 | 290 | 5300 |
| | 36° C. | 522 | 410 | 548 | 552 | 359 | 1060 | 1170 | 6470 |
| | 38° C. | 744 | 648 | 601 | 647 | 430 | 1260 | 1270 | 9820 |
| | 40° C. | 828 | 741 | 605 | 657 | 492 | 1350 | 1440 | 3420 |

TABLE 4

| (w/v %) | | Ex. 11 | Ex. 12 | Ex. 13 | Ex. 14 | Ex. 15 | Ex. 16 | Ex. 17 | Ex. 18 | Ex. 19 | Ex. 20 | Ex. 21 |
|---|---|---|---|---|---|---|---|---|---|---|---|---|
| Methyl Cellulose (SM-4) | | 1.3 | 1.3 | 1.3 | 1.3 | 1.3 | 1.0 | 1.3 | 1.5 | 2.0 | 1.0 | 1.5 |
| Methyl Cellulose (SM-15) | | 1.2 | 1.2 | 1.2 | 1.2 | 1.2 | 1.0 | 1.2 | 1.5 | 2.0 | 1.0 | 1.5 |
| Sodium Citrate Hydrate | | 2.2 | 2.2 | 2.2 | 1.0 | 2.2 | 1.0 | 2.2 | 2.2 | 1.0 | 2.2 | 2.0 |
| PVP k25 | | 0.5 | 2.0 | 2.0 | 2.0 | 0.5 | — | — | — | — | — | — |
| PVP k30 | | — | — | — | — | — | 2.0 | — | 2.0 | 2.5 | 0.5 | 2.5 |
| PVP k90 | | — | — | — | — | — | — | 0.5 | — | — | — | — |
| Benzalkonium Chloride | | 0.005 | 0.005 | 0.005 | 0.005 | 0.005 | 0.005 | 0.005 | 0.005 | 0.005 | 0.005 | 0.005 |
| Polyethylene Glycol 8000 | | 2.0 | 0.5 | 4.0 | 4.0 | 4.0 | 2.0 | 2.0 | 0.5 | 2.0 | 4.0 | 0.5 |
| pH Adjuster | | q.s. | q.s. | q.s. | q.s. | q.s. | q.s. | q.s. | q.s. | q.s. | q.s. | q.s. |
| pH | | 7.0 | 7.0 | 7.0 | 7.0 | 7.0 | 7.0 | 7.0 | 7.0 | 7.0 | 7.0 | 7.0 |
| Viscosity (mPa · s) | 20° C. | 17.5 | 17.5 | 27.3 | 26.6 | 24.0 | 14.6 | 26.4 | 26.8 | 64.2 | 16.4 | 28.7 |
| | 24° C. | 15.1 | 15.2 | 23.6 | 23.1 | 19.3 | 12.6 | 22.6 | 23.3 | 55.3 | 14.1 | 24.7 |
| | 28° C. | 13.1 | 13.4 | 21.6 | 20.5 | 16.9 | 11.1 | 19.9 | 21 | 49 | 12.8 | 22.2 |
| | 32° C. | 12.3 | 12.5 | 29.7 | 20.2 | 12.5 | 10.0 | 22.5 | 28.3 | 50 | 14.3 | 24.6 |
| | 34° C. | 15.5 | 14.6 | 403 | 26.7 | 78.6 | 10.3 | 56.3 | 79.2 | 92.9 | 42.1 | 60.6 |
| | 36° C. | 67.5 | 45.3 | 1350 | 62.9 | 375 | 19.5 | 321 | 487 | 427 | 178 | 315 |
| | 38° C. | 857 | 299 | 804 | 188 | 619 | 42.8 | 514 | 742 | 1520 | 395 | 1440 |
| | 40° C. | 870 | 512 | 727 | 712 | 773 | 107 | 926 | 905 | 2260 | 507 | 1300 |

TABLE 5

| (w/v %) | | Ex. 22 | Ex. 23 | Ex. 24 | Ex. 25 |
|---|---|---|---|---|---|
| Methyl Cellulose (SM-4) | | 1.3 | 1.3 | 1.3 | 1.3 |
| Methyl Cellulose (SM-15) | | 1.2 | 1.2 | 1.2 | 1.2 |
| Sodium Citrate Hydrate | | 2.2 | 2.2 | 2.2 | 2.2 |
| PVP k25 | | 2.0 | 2.0 | 2.0 | 2.0 |
| Benzethonium Chloride | | 0.005 | — | — | — |
| Chlorhexidine Gluconate | | — | 0.002 | — | — |
| Polidronium Chloride | | — | — | 0.005 | — |
| Methyl Parahydroxybenzoate | | — | — | — | 0.026 |
| Propyl Parahydroxybenzoate | | — | — | — | 0.014 |
| Polyethylene Glycol 8000 | | 2.0 | 2.0 | 2.0 | 2.0 |
| pH Adjuster | | q.s. | q.s. | q.s. | q.s. |
| pH | | 7.0 | 7.0 | 7.0 | 5.0 |
| Viscosity (mPa · s) | 20° C. | 20.4 | 23.4 | 26.3 | 23 |
| | 24° C. | 17.7 | 19.9 | 22 | 20.9 |
| | 28° C. | 15.4 | 18.6 | 30.2 | 22.6 |

TABLE 5-continued

| (w/v %) | | Ex. 22 | Ex. 23 | Ex. 24 | Ex. 25 |
|---|---|---|---|---|---|
| | 32° C. | 14.8 | 34.2 | 44.4 | 61 |
| | 34° C. | 22.5 | 125 | 111 | 161 |
| | 36° C. | 184 | 463 | 283 | 512 |
| | 38° C. | 1160 | 689 | 640 | 666 |
| | 40° C. | 797 | 872 | 824 | 775 |

TABLE 6

| (w/v %) | | Ex. 26 | Ex. 27 | Ex. 28 | Ex. 29 | Ex. 30 | Ex. 31 | Ex. 32 | Ex. 33 |
|---|---|---|---|---|---|---|---|---|---|
| Methyl Cellulose (SM-4) | | 0.5 | 2.0 | 1.25 | 1.25 | 1.25 | 1.25 | 1.3 | 1.3 |
| Methyl Cellulose (SM-15) | | 2.0 | 0.5 | 1.25 | 1.25 | 1.25 | 1.25 | 1.2 | 1.2 |
| Sodium Citrate Hydrate | | 2.5 | 2.5 | 3.0 | 3.0 | 3.0 | 3.0 | 2.2 | 2.2 |
| PVP k25 | | 2.5 | 2.5 | 2.5 | 2.5 | 2.5 | 2.5 | 2.0 | 2.0 |
| Boric Acid | | — | — | 0.5 | — | — | — | — | — |
| Taurine | | — | — | — | 0.7 | — | — | — | — |
| Hyaluronic Acid | | — | — | — | — | 0.02 | — | — | — |
| Trometamol | | — | — | — | — | — | 1.0 | — | — |
| Benzalkonium Chloride | | 0.002 | 0.002 | 0.002 | 0.002 | 0.002 | 0.002 | 0.002 | 0.002 |
| Polyethylene Glycol 4000 | | 1.0 | 2.0 | 0.5 | 0.5 | 0.5 | 0.5 | — | — |
| Polyethylene Glycol 400 | | — | — | — | — | — | — | 2.0 | — |
| Polyethylene Glycol 300 | | — | — | — | — | — | — | — | 2.0 |
| pH Adjuster | | q.s. | q.s. | q.s. | q.s. | q.s. | q.s. | q.s. | q.s. |
| pH | | 7.0 | 7.0 | 7.0 | 7.0 | 7.0 | 7.0 | 7.0 | 7.0 |
| Viscosity | 20° C. | 30 | 14.8 | 22.1 | 23.2 | 30.1 | 16.3 | 20.8 | 24.2 |
| (mPa · s) | 24° C. | 26 | 12.9 | 18.2 | 21.2 | 25.5 | 14.1 | 18.7 | 19.5 |
| | 28° C. | 23.2 | 12 | 16.9 | 21.4 | 25.1 | 12.2 | 18.8 | 20.5 |
| | 32° C. | 27.4 | 17.9 | 23 | 38.3 | 124 | 13.7 | 25.1 | 28.1 |
| | 34° C. | 78.9 | 181 | 110 | 451 | 572 | 51 | 59.9 | 52.0 |
| | 36° C. | 498 | 488 | 538 | 659 | 629 | 297 | 166 | 148 |
| | 38° C. | 590 | 563 | 655 | 651 | 599 | 518 | 563 | 392 |
| | 40° C. | 749 | 529 | 676 | 686 | 487 | 500 | 649 | 803 |

TABLE 7

| (w/v %) | | Ex. 34 | Ex. 35 | Ex. 36 | Ex. 37 | Ex. 38 | Ex. 39 |
|---|---|---|---|---|---|---|---|
| Methyl Cellulose (SM-4) | | 1.3 | 1.3 | 1.3 | 1.3 | 1.3 | 1.3 |
| Methyl Cellulose (SM-15) | | 1.2 | 1.2 | 1.2 | 1.2 | 1.2 | 1.2 |
| Sodium Citrate Hydrate | | 2.2 | 1.0 | 2.2 | 1.0 | 2.2 | 1.0 |
| PVP k25 | | 2.0 | 2.0 | 2.0 | 2.0 | 2.0 | 2.0 |
| NaCl | | 0.3 | 0.5 | — | — | — | — |
| KCl | | — | — | 0.2 | 0.6 | — | — |
| Sodium Hydrogen Carbonate | | — | — | — | — | 0.1 | 0.7 |
| Benzalkonium Chloride | | 0.002 | 0.002 | 0.002 | 0.002 | 0.002 | 0.002 |
| Polyethylene Glycol 4000 | | 2.0 | 2.0 | 2.0 | 2.0 | 2.0 | 2.0 |
| pH Adjuster | | q.s. | q.s. | q.s. | q.s. | q.s. | q.s. |
| pH | | 7.0 | 7.0 | 7.0 | 7.0 | 7.0 | 7.0 |
| Viscosity | 20° C. | 19.6 | 18.3 | 25.3 | 19.9 | 20.3 | 16.4 |
| (mPa · s) | 24° C. | 16.9 | 15.9 | 21.4 | 16.1 | 17.2 | 14.2 |
| | 28° C. | 15.1 | 13.9 | 18.1 | 15.6 | 16.7 | 12.5 |
| | 32° C. | 16.3 | 12.7 | 37.5 | 20.8 | 22.2 | 11.4 |
| | 34° C. | 48.7 | 13.4 | 44.4 | 51 | 52.2 | 12.2 |
| | 36° C. | 851 | 21.7 | 163 | 60.3 | 196 | 18.6 |
| | 38° C. | 932 | 71.6 | 646 | 145 | 713 | 76.0 |
| | 40° C. | 649 | 327 | 757 | 290 | 746 | 443 |

Tables 3 to 7 show that Examples 4 to 39 being the compositions of the present invention maintained a low viscosity until 32° C., and the viscosity suddenly increased between 34° C. and 40° C.

Table 3 shows that the compositions of the present invention can be prepared regardless of the type of MC and have a thermo-responsive gelling property.

When comparing Example 8 and Example 9 of Table 3, it is apparent that the viscosity at low temperatures increases as the ratio of MC having a large label viscosity increases.

Table 4 shows that the compositions of the present invention can be prepared regardless of the type of PVP or of the weight average molecular weight and have a thermo-responsive gelling property.

Comparison of Example 13 and Example 14 of Table 4 shows that the viscosity increases gently at 34 to 40° C. for compositions having a lower concentration of sodium citrate.

Comparison of Example 12 and Example 13 of Table 4 shows that the viscosity increases gently at 34 to 40° C. for compositions having a lower concentration of polyethylene glycol.

Comparison of Example 13 and Example 15 of Table 4 shows that the viscosity increases gently at 34 to 40° C. for compositions having a lower concentration of PVP.

From Table 5, it is apparent that it is possible to add various types of antiseptics to the compositions of the present invention, which does not affect the thermo-responsive gelling property.

From Table 6, it is apparent that it is possible to add acids such as boric acid, additives which increses viscosity such as hyaluronic acid, bases such as trometamol, and amino acids such as taurine to the compositions of the present invention, which does not affect the thermo-responsive gelling property.

Table 6 shows that the compositions of the present invention can be prepared regardless of the type of polyethylene glycol or of the weight average molecular weight and have a thermo-responsive gelling property.

From Table 7, it is apparent that it is possible to add various types of inorganic salts to the compositions of the present invention, which does not affect the thermo-responsive gelling property.

and have retention because they respond to the temperature of the ocular surface after application to immediately increases viscosity.

TEST EXAMPLE 1C

Examples 40 to 52 were prepared in the same procedures as those of Examples 1 and 2 described above to measure the viscosity at 20° C. to 40° C. Table 8 shows the formulation content and the measurement results.

TABLE 8

| (w/v %) | | Ex. 40 | Ex. 41 | Ex. 42 | Ex. 43 | Ex. 44 | Ex. 45 | Ex. 46 |
|---|---|---|---|---|---|---|---|---|
| Methyl Cellulose (SM-4) | | 0.3 | 0.5 | 1.5 | 1.5 | 1.0 | 0.8 | 2.0 |
| Methyl Cellulose (SM-15) | | 0.3 | 0.5 | 1.5 | 1.5 | 1.0 | 0.8 | 2.0 |
| Sodium Citrate Hydrate | | 4.0 | 4.0 | 2.2 | 2.2 | 3.5 | 4.0 | 0.5 |
| PVP k25 | | 4.0 | 2.0 | 2.0 | 2.0 | 2.0 | 2.0 | 3.0 |
| Polyethylene Glycol 8000 | | 0.5 | 0.5 | 2.0 | 2.0 | 1.0 | 0.5 | 4.0 |
| Polyethylene Glycol 400 | | — | — | — | — | — | — | — |
| Polypropylene Glycol 400 | | — | — | — | — | — | — | — |
| Benzalkonium Chloride | | 0.002 | 0.002 | 0.002 | 0.002 | 0.002 | 0.002 | 0.002 |
| pH Adjuster | | q.s. | q.s. | q.s. | q.s. | q.s. | q.s. | q.s. |
| pH | | 7.0 | 7.0 | 6.0 | 8.0 | 7.0 | 7.0 | 7.0 |
| Viscosity (mPa · s) | 20° C. | 7.74 | 5.56 | 30.7 | 32.6 | 15.2 | 10.3 | 88.5 |
| | 24° C. | 7.48 | 4.75 | 26.3 | 27.7 | 12.1 | 8.15 | 71.8 |
| | 28° C. | 5.48 | 4.25 | 22.1 | 24.6 | 10 | 6.79 | 62.2 |
| | 32° C. | 5.73 | 7.59 | 22.0 | 35.8 | 13.1 | 18 | 60.4 |
| | 34° C. | 11.0 | 40.2 | 57.0 | 135.0 | 52.9 | 95.1 | 85.5 |
| | 36° C. | 33.1 | 75.3 | 180.0 | 1290.0 | 197 | 100 | 209 |
| | 38° C. | 24.3 | 45.8 | 1120.0 | 1990.0 | 255 | 81.6 | 919 |
| | 40° C. | 21.9 | 37.6 | 1720.0 | 1050.0 | 222 | 78.8 | 3470 |

| (w/v %) | | Ex. 47 | Ex. 48 | Ex. 49 | Ex. 50 | Ex. 51 | Ex. 52 |
|---|---|---|---|---|---|---|---|
| Methyl Cellulose (SM-4) | | 2.0 | 1.0 | 1.0 | 1.3 | 1.3 | 1.3 |
| Methyl Cellulose (SM-15) | | 2.0 | 1.0 | 1.0 | 1.2 | 1.2 | 1.2 |
| Sodium Citrate Hydrate | | 0.8 | 2.0 | 2.0 | 2.2 | 2.2 | 2.2 |
| PVP k25 | | 3.0 | 4.0 | 4.0 | 2.0 | 2.0 | 2.0 |
| Polyethylene Glycol 8000 | | 4.0 | 1.0 | 2.0 | — | — | 1.0 |
| Polyethylene Glycol 400 | | — | — | — | — | 1.0 | — |
| Polypropylene Glycol 400 | | — | — | — | 2.0 | 1.0 | 1.0 |
| Benzalkonium Chloride | | 0.002 | 0.002 | 0.002 | 0.002 | 0.002 | 0.002 |
| pH Adjuster | | q.s. | q.s. | q.s. | q.s. | q.s. | q.s. |
| pH | | 7.0 | 7.0 | 7.0 | 7.0 | 7.0 | 7.0 |
| Viscosity (mPa · s) | 20° C. | 82.3 | 17.5 | 20.7 | 17.0 | 18.0 | 19.0 |
| | 24° C. | 67.9 | 14.5 | 17.5 | 14.6 | 15.3 | 16.5 |
| | 28° C. | 60.5 | 13.2 | 15.6 | 12.6 | 13.3 | 14.3 |
| | 32° C. | 80.7 | 14.6 | 19.7 | 10.9 | 12.3 | 13.6 |
| | 34° C. | 289 | 16.2 | 58.2 | 11.2 | 15.8 | 18.9 |
| | 36° C. | 1340 | 45.5 | 240 | 14.4 | 59.8 | 91.6 |
| | 38° C. | 2480 | 125 | 791 | 69.9 | 430.0 | 741.0 |
| | 40° C. | 2210 | 368 | 701 | 435.0 | 1160 | 792 |

From Table 4, it is apparent that sodium citrate and polyethylene glycol affect the increase in viscosity of the compositions of the present invention attributed to heat.

From Table 4, it is apparent that PVP affects the increase in viscosity of the compositions of the present invention attributed to heat, not as much as the sodium citrate or the polyethylene glycol described above.

Since Table 5 shows that it is possible to add antiseptics regardless of the type thereof, it is shown that the present invention is suitable as an aqueous medical composition.

Table 6 and Table 7 show that the compositions of the present invention are suitable as a composition for artificial lacrima.

Tables 3 to 7 show that the compositions of the present invention can be stored as a liquid which can be readily administered at room temperature (1 to 30° C.).

Tables 3 to 7 suggest that the compositions of the present invention are suitable as an ophthalmic aqueous composition Although Examples 40, 42, and 46 have a low viscosity around 20 to 32° C., the viscosity increases around the body temperature of 36 to 40° C.

Although Examples 49, 51, and 52 have a low viscosity around 20 to 34° C., the viscosity increases at 38 and 40° C.

In consideration of the viscosity behavior observed in the viscosity measurement of this test, it has been shown that Examples 40 to 52 also have the characteristics of the present invention because they have the same viscosity transition as that of other examples of the present invention.

TEST EXAMPLE 2

Investigation was carried out on thixotropy at the time of gelation for Example 2 shown in Table 1 and Comparative Examples 2 to 4 shown in Table 2.

As regards the compositions of Example 2 and Comparative Examples 2 to 4, the relationship between shear stress and strain was obtained for the compositions after gelation by use of a rheometer manufactured by Anton-Paar (Modular Compact Rheometer 102). The evaluation was carried out such that thixotropy was possessed if there was a point at which the shear stress is not in a proportional relationship to the strain when increased.

Figure 2:
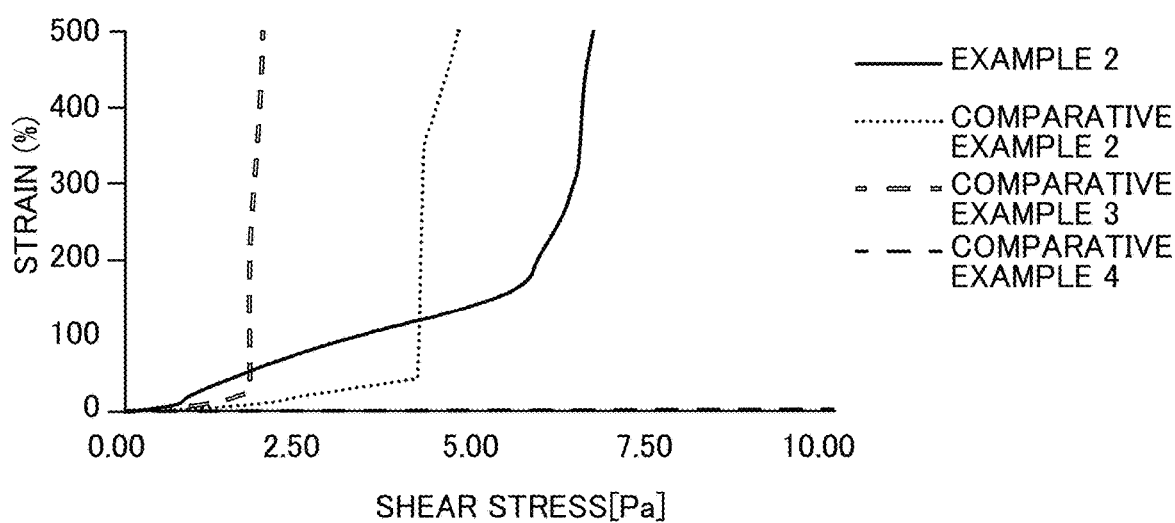
FIG. 2 shows thixotropy in Examples and Comparative Examples of the present invention.

About 1 mL of the prepared compositions of the present invention and Comparative Examples was set between a parallel plate having a diameter of about 50 mm and a temperature control peltier. The gap between the peltier and the parallel plate was set to 0.5 mm Before the start of measurement, the measurement sample was kept cool at 5° C. for 5 minutes. From the start of measurement, the compositions were retained at 36° C. for about 10 minutes. Next, after retention at 25° C. for 240 seconds, the strain was obtained by vibration measurement for the case where the frequency was 1 (Hz) and the shear stress was changed from 0.01 to 10 Pa. FIG. 2 shows the results.

The results show that Examples being the compositions of the present invention and Comparative Examples 2 and 3 each have thixotropy because there is a point (yield stress) at which the stress and the strain are not in a proportional relationship. Comparative Example 4 was shown to have no thixotropy because there was no yield stress under the present test conditions.

TEST EXAMPLE 3A

As regards Examples 1 and 2 shown in Table 1 and Comparative Examples 1 to 3 shown in Table 2, reproducibility was evaluated by measuring the viscosity through repetition of heating and cooling over a predetermined period of time.

Figure 3:
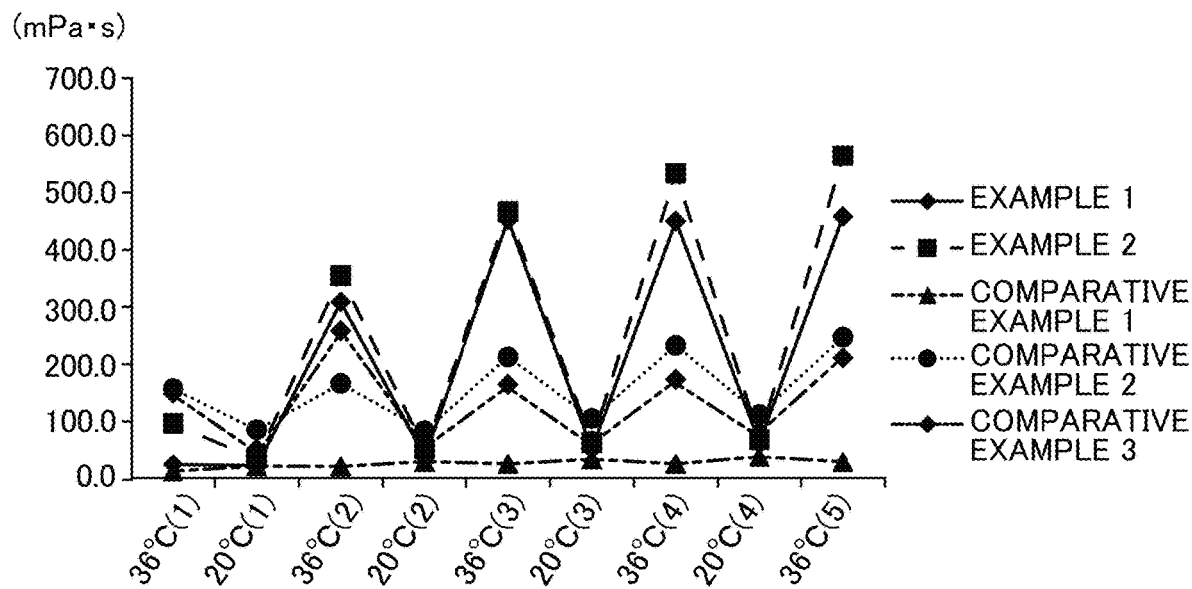
FIG. 3 is a graph showing thermal responsiveness in Examples and Comparative Examples of the present invention.

As regards Example 2 being a composition of the present invention, the viscosity was evaluated at 20° C. and 36° C. when altering temperature repeatedly. The viscosity was measured with a rheometer manufactured by Anton-Paar (Modular Compact Rheometer 102). About 1 mL of the prepared compositions of the present invention was set between a parallel plate having a diameter of about 50 mm and a temperature control peltier. The gap between the peltier and the parallel plate was set to 0.5 mm. Before the start of measurement, the measurement sample was kept cool at 5° C. for 10 minutes. Once the measurement was started, the temperature was caused to rise to 36° C. and was kept for 240 seconds, and then the viscosity was measured. Next, the temperature was cooled to 20° C. and was kept for 240 seconds, and then the viscosity was measured. This operation between 36° C. and 20° C. was repeated 4 times and a half. In Comparative Example 4, the viscosity at 36° C. was very high and measurement under the same conditions as those of other samples was impossible. Thus, FIG. 3 shows the results of Examples 1 and 2 and Comparative Examples 1 to 3.

In Examples 1 and 2 being the compositions of the present invention, in the second to fifth operations, the viscosity increased and exhibited 300 to 600 mPa·s at 36° C., and the viscosity exhibited 100 mPa·s or less at 20° C. Thermal responsiveness was maintained even when the operation of heating and cooling was repeated 4 times or more. It is shown that the property of increasing viscosity at 36° C. is maintained for the compositions of the present invention compared to Comparative Examples 1 to 3.

TEST EXAMPLE 3B

As regards Examples 9 and 10 shown in Table 3, reproducibility was evaluated by measuring the viscosity through repetition of heating and cooling over a predetermined period of time.

Figure 4:
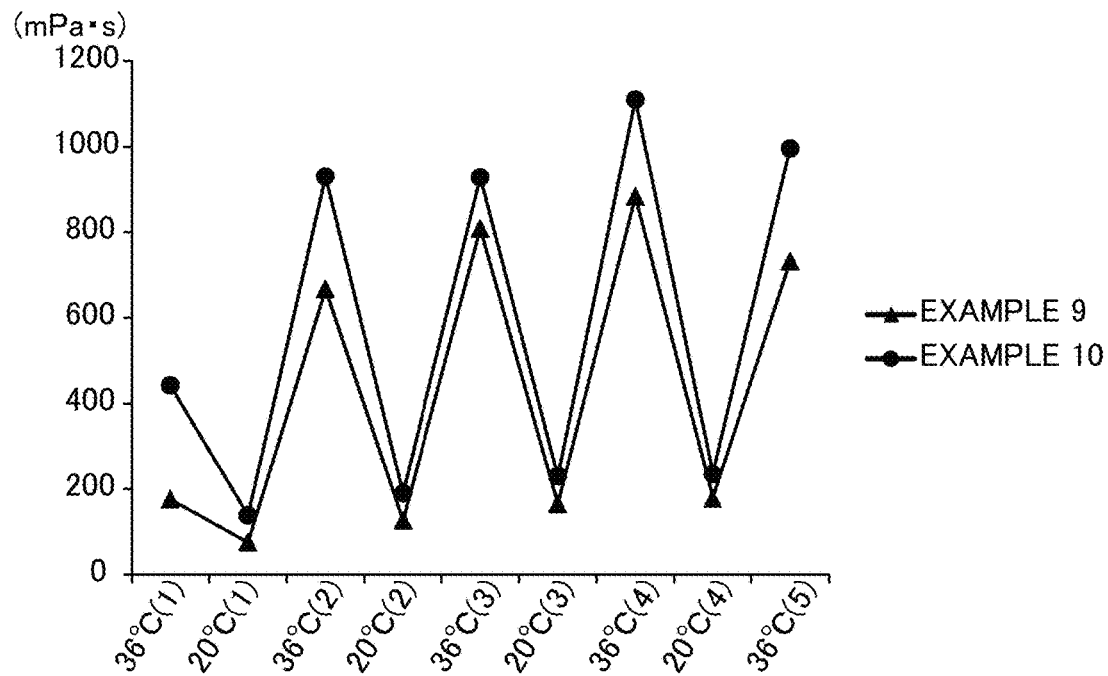
FIG. 4 is a graph showing thermal responsiveness in Examples of the present invention.

The test operations are the same as those in Test Example 3A. FIG. 4 shows the results.

The test results of Test Example 3B show that Examples of the present invention maintain thermal responsiveness even when the operation of heating and cooling was repeated.

TEST EXAMPLE 4

Investigation was carried out on the relationship between temperature and solution state (sol and gel) for Example 2 shown in Table 1 and Comparative Examples 1 to 4 shown in Table 2, and the gelation reproducibility of each aqueous composition was obtained.

As regards the compositions of Example 2 and Comparative Examples 1 to 4, evaluation was carried out on the solution state (sol and gel) relationship when the temperature was caused to rise from 30° C. to 36° C. and the gelation reproducibility after the gel structure was destructed at 30° C. A rheometer manufactured by Anton-Paar (Modular Compact Rheometer 102) was used to measure by vibration measurement a storage elastic modulus (G') and a loss elastic modulus (G") being gelation indices, and then the value of a loss tangent ($\tan(\delta)$) determined by the formula G"/G' was obtained. In general, it is said that one showing $\tan(\delta)>1$ is a sol and one showing $\tan(\delta)<1$ is a gel (Gel Control—How to Make Gel Skillfully and Suppression of Gelation—, June 2009, published by: JOHOKIKO CO., LTD.).

Figure 5:
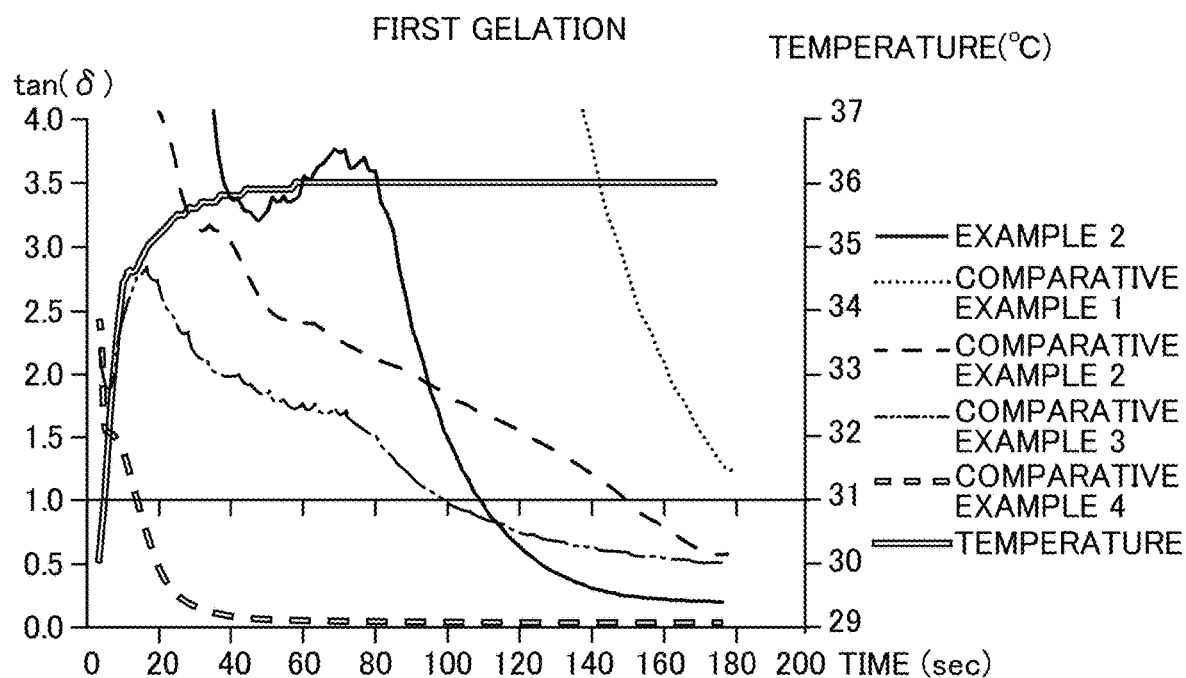
FIG. 5 is a graph showing gelation behavior (first) in Examples and Comparative Examples of the present invention.
Figure 6:
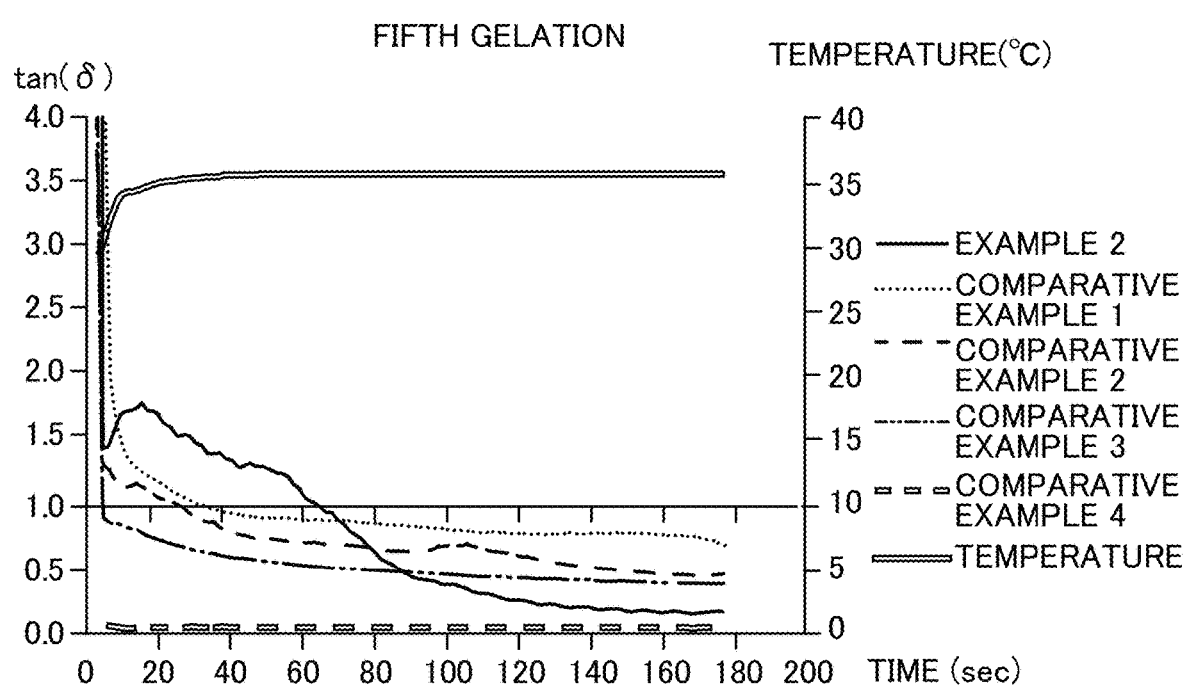
FIG. 6 is a graph showing reproducibility for gelation (fifth) in Examples and Comparative Examples of the present invention.
Figure 7:
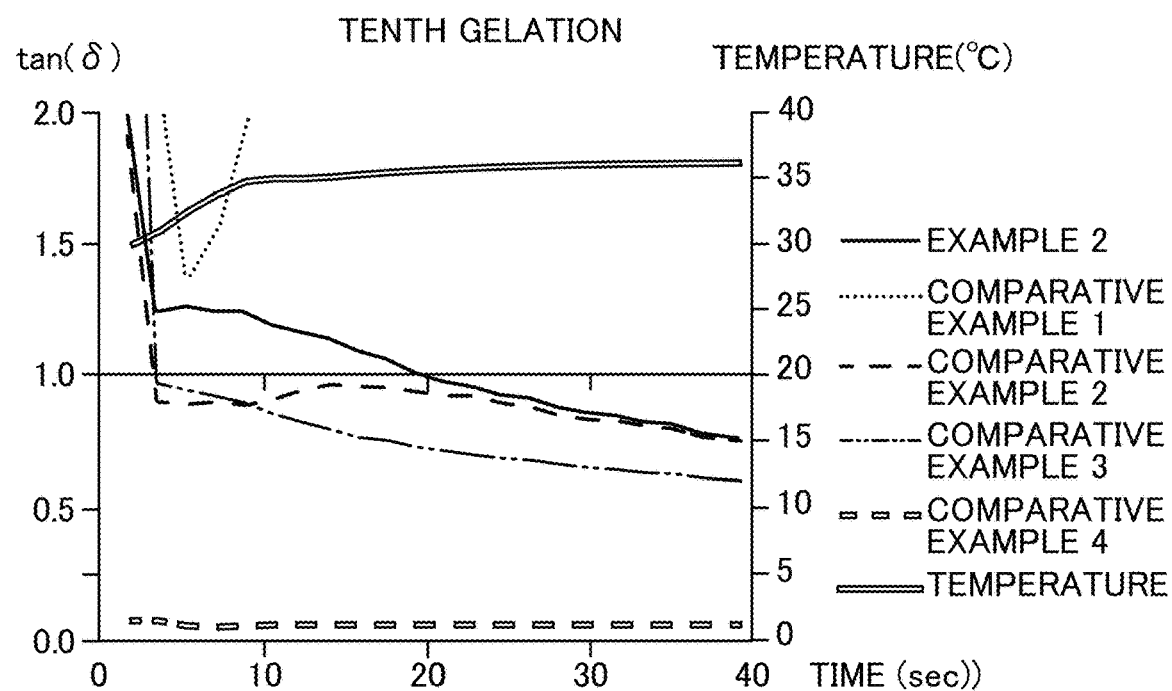
FIG. 7 is a graph showing reproducibility for gelation (10th) in Examples and Comparative Examples of the present invention.

About 1 mL of prepared Examples of the present invention and Comparative Examples was set between a parallel plate having a diameter of about 50 mm and a temperature control peltier. The gap between the peltier and the parallel plate was set to 0.5 mm. Before the start of measurement, the measurement sample was kept cool at 5° C. for 10 minutes. From the start of measurement, the temperature was caused to rise to 30° C. in about 1 minute, and the compositions were retained for about 30 seconds. Vibration measurement was carried out under the test conditions of a frequency of 1 (Hz) and a strain of 5%. Next, the temperature of the measurement sample was caused to rise to 36° C. in about 30 seconds, and then the temperature was maintained for about 150 seconds. After that, the parallel plate was rotated under the conditions of 30° C. and a shear stress of 10 Pa to destruct the gel structure. The measurement was carried out while causing the temperature to rise to 36° C. The above operations were repeated 10 times. FIGS. 5 to 7 show the gelation behavior at the first time and the results of evaluation of the gelation reproducibility at the fifth time and the 10th time.

In the measurement of gelation at the first time, Comparative Example 4 was satisfied with $\tan(\delta)<1$ earliest and gelated. After that, it turned out that Comparative Example 3, Example 2, and Comparative Example 2 gelated in this order, and Comparative Example 1 did not gelated within this period of time. The order of gelation among these compositions was almost coincided with the viscosities at 36° C. of Test Example 1.

In the evaluation of gelation reproducibility, in Comparative Examples 1 to 4, transition into sol became worse as the operation was repeated. Although transition into sol became weaker in Example 2, it maintained the sol state for a period of time longer than Comparative Examples even at the tenth operation.

These results showed that in Examples of the present invention, mixing of two types of methyl celluloses in an appropriate ratio resulted in good gelation reproducibility.

The results of Test Examples 3A, 3B, and 4 show that the characteristics of the present invention are obtained by mixing MCs having different label viscosities for preparation.

TEST EXAMPLE 5

A Evaluation of Cornea Protection Function (1) Sample Solution

Example 3, Comparative Example 5, and Comparative Example 6 of Table 9 were prepared in the same manner as Test Example 1. Isotonic sodium chloride solution (HIKARI PHARMACEUTICAL CO., LTD.) (hereinafter also referred to as saline) was used for comparison.

TABLE 9

| (w/v %) | Ex. 3 | Comp. Ex. 5 BAC is added to Formulation No. 1 of Patent Literature 4 | Comp. Ex. 6 BAC is added to Example-3 of Patent Literature 5 |
|---|---|---|---|
| Methyl Cellulose (SM-4) | 1.3 | 1.2 | — |
| Methyl Cellulose (SM-15) | 1.2 | — | — |
| Methyl Cellulose (SM-100) | — | — | 0.5 |
| Methyl Cellulose (SM-400) | — | — | 0.1 |
| Hydroxyethyl Cellulose | — | — | 2.0 |
| Polyethylene Glycol 4000 | — | 2.0 | — |
| Polyethylene Glycol 8000 | 2.0 | — | — |
| Sodium Citrate | 2.2 | 3.5 | — |
| PVP k25 | 2.0 | — | 3.0 |
| D-Mannitol | — | 0.8 | — |
| pH Adjuster | q.s. | q.s. | q.s. |
| Benzalkonium Chloride | 0.002 | 0.002 | 0.002 |
| pH | 7.0 | 7.0 | 7.0 |
| Gelation Temperature | 34 | 28 | — |
| Thixotropy | Yes | Yes | — |

(2) Testing Method

Pigmented rabbits (strain; Kbt: Dutch, weight at the time of transfer 1.5 to 2.0 kg, Biotech) were euthanatized to sample the cornea (n=3). After that, the sampled cornea was dried inside an incubator at 35° C. for 40 minutes. Immediately after the start of drying, Example 3 and saline which had been stored at room temperature, and Comparative Example 5 and Comparative Example 6 which had been stored at 5° C. and returned to room temperature immediately before use were added dropwise onto the sampled cornea at an interval of 1 minute, each in an amount of 10 μL×6 times (60 μL in total). After drying, the cornea was washed with saline, stained with 1% methylene blue (Nacalai Tesque), immersed in 400 μL of extraction liquids (acetone (Wako Pure Chemical Industries): saturated sodium sulfate (Wako Pure Chemical Industries) aqueous solution=7:3, volume ratio) for a whole day and night or more to extract methylene blue remaining in the cornea. Then, the absorbance at 660 nm for each extraction liquid was measured.

Figure 8:
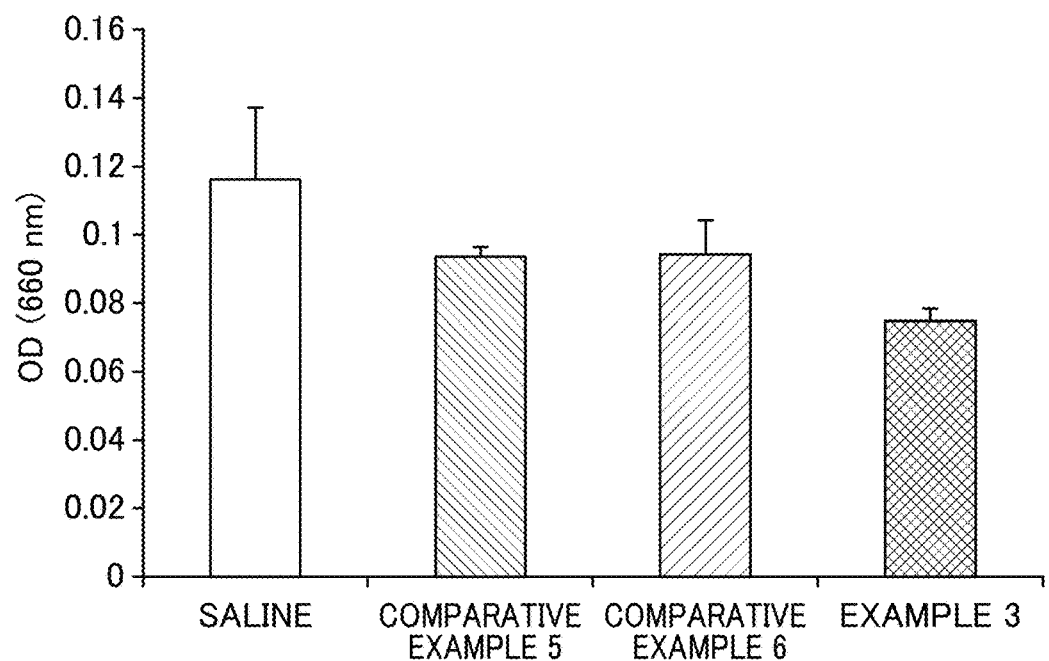
FIG. 8 is a graph showing results of evaluating a cornea protection function in Examples and Comparative Examples of the present invention.

FIG. 8 shows the results.

The results were such that the absorbance of Example 3 of the present invention was lower than Comparative Example 5 and Comparative Example 6 or isotonic sodium chloride solution.

The results of Test Example 5A showed that Example 3 of the present invention has a characteristic of more suppressing the drying of the cornea than saline or the existing thermo-responsive gelling formulations, Comparative Example 5 and Comparative Example 6.

Thus, the compositions of the present invention were shown to have a cornea protection function.

TEST EXAMPLE 5

B Evaluation 2 of Cornea Protection Function (1) Sample Solution

Comparative Example 5 of Table 9, Example 17 of Table 4, and Example 32 of Table 6 were prepared in the same manner as Test Example 1. Isotonic sodium chloride solution (HIKARI PHARMACEUTICAL CO., LTD.) was used for comparison.

(2) Testing Method

Figure 9:
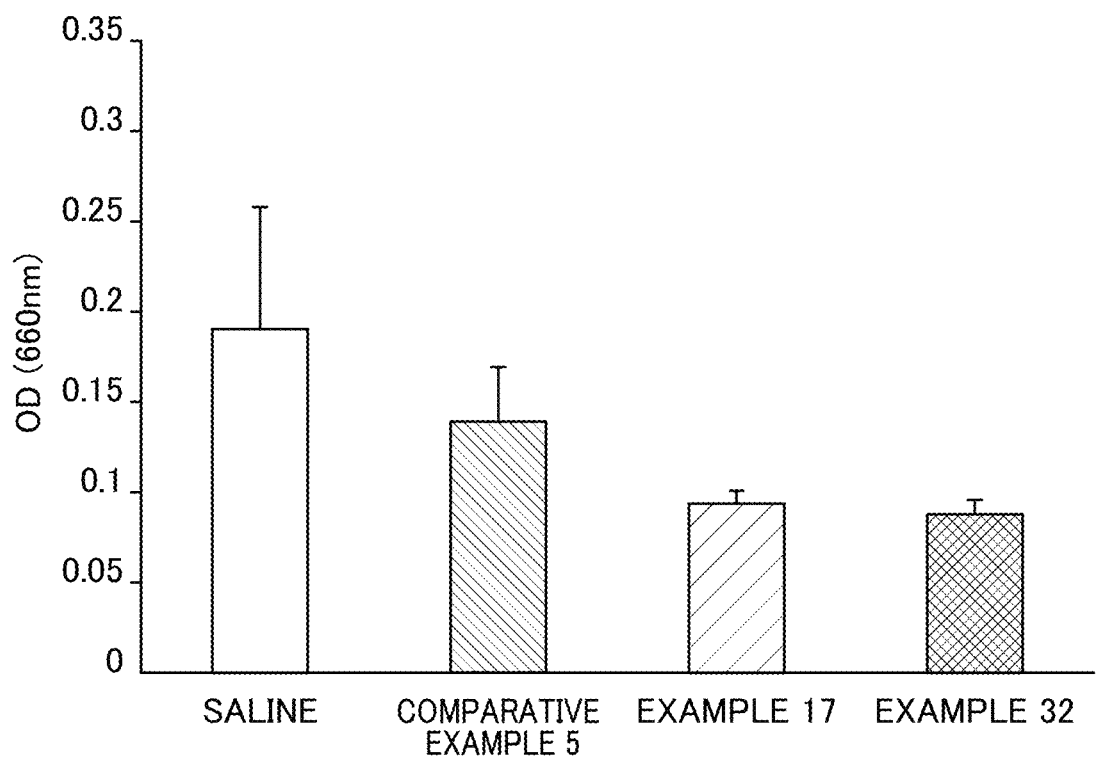
FIG. 9 is a graph showing results of evaluating a cornea protection function in Examples and Comparative Examples of the present invention.

Pigmented rabbits (strain; Kbt: Dutch, weight at the time of transfer 1.5 to 2.0 kg, Biotech) were euthanatized to sample the cornea. After that, the sampled cornea was added dropwise with 150 μL of each of Example 17, Example 32, and Comparative Example 5 and was dried inside an incubator at 35° C. for 40 minutes. After drying, the cornea was washed with saline, stained with 1% methylene blue (Nacalai Tesque), immersed in 400 μL of extraction liquids (acetone (Wako Pure Chemical Industries): saturated sodium sulfate (Wako Pure Chemical Industries) aqueous solution=7:3, volume ratio) for a whole day and night or more to extract methylene blue remaining in the cornea. Then, the absorbance at 660 nm for each extraction liquid was measured. FIG. 9 shows the results.

Example 17 and Example 32 of the present invention exhibited an absorbance lower than those of Comparative Example 5 or saline.

The results of Test Example 5B showed that Examples of the present invention have a characteristic of more suppressing the drying of the cornea than the saline or the existing thermo-responsive gelling formulations, Comparative Example 5.

Thus, the compositions of the present invention were shown to have a cornea protection function.

TEST EXAMPLE 6

Comparison of Cornea Protection Function in Present Invention and Existing Products (1) Sample Solution As an example, Example 3 of Table 9 was prepared in the same manner as Test Example 1.

As a comparative example, SYSTANE (registered trademark) ULTRA manufactured by Novartis Pharma K.K. was used as Comparative Example A. Additionally, SYSTANE (registered trademark) GEL DROPS manufactured by the same company was used as Comparative Example B. Isotonic sodium chloride solution (HIKARI PHARMACEUTICAL CO., LTD.) was used for comparison.

(2) Testing Method

Albino rabbits (strain; Kbs: JW, weight of 3.5 kg or more, KITAYAMA LABES CO., LTD.) were euthanatized to sample the cornea (n=3 to 7). After that, 150 μL of each of saline, Example 3, Comparative Example A, and Comparative Example B was added dropwise onto the cornea. After dropping, the cornea was dried inside an incubator at 35° C. for 40 to 50 minutes. After drying, the cornea was washed with saline, stained with 1% methylene blue (Nacalai Tesque), immersed in 400 μL of extraction liquids (acetone (Wako Pure Chemical Industries): saturated sodium sulfate (Wako Pure Chemical Industries) aqueous solution=7:3, volume ratio) for a whole day and night or more to extract methylene blue remaining in the cornea. Then, the absorbance at 660 nm for each extraction liquid was measured.

Figure 10:
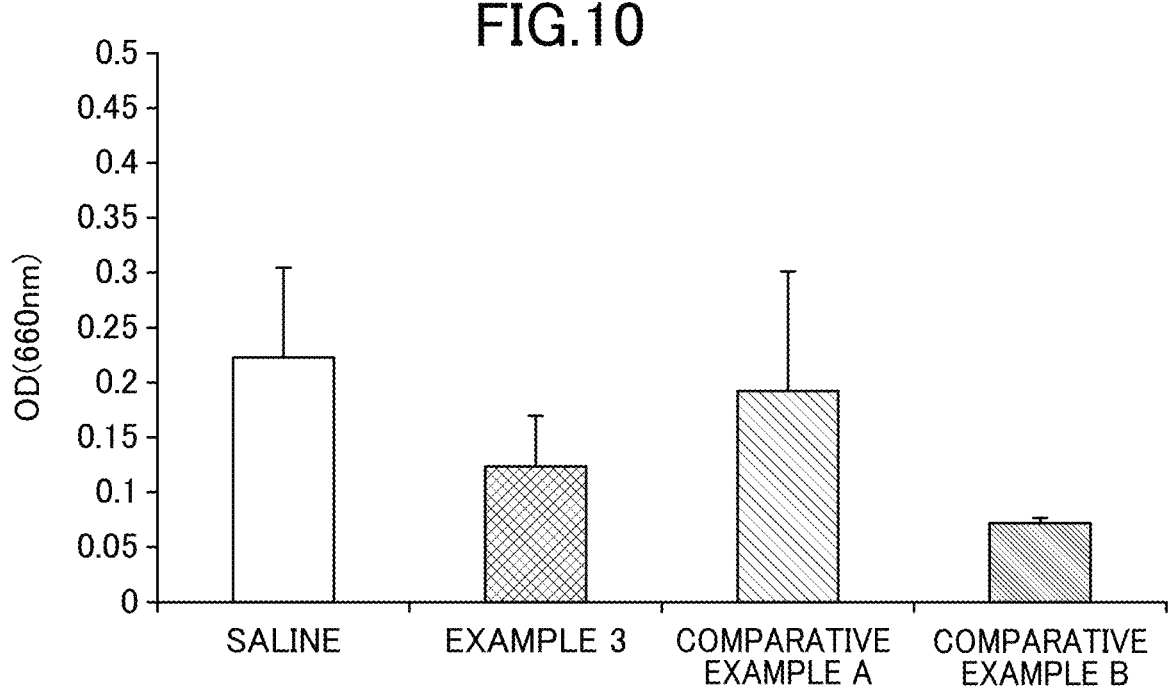
FIG. 10 is a graph showing results of evaluating a cornea protection function in Examples and Comparative Examples of the present invention.

FIG. 10 shows the results.

The absorbance of Example 3 of the present invention was lower than Comparative Example A and equal to or more than Comparative Example B.

The results of Test Example 6 suggest that the ophthalmic aqueous compositions of the present invention have an effect of preventing dysfunctions equal to or better than non-viscous aqueous formulations.

TEST EXAMPLE 7

Comparison of Ocular Surface Retention in Present Invention and Commercial Products (1) Sample Solution As an example, Example 2 of Table 1 was prepared in the same manner as Test Example 1, and an installation bottle was filled.

As a comparative example, Comparative Example A and Comparative Example B were used in the same manner as Test Example 6.

FLUORESCITE (registered trademark) intravenous injection (500 mg) was added to these sample solutions to obtain 1 mg/mL.

(2) Testing Method

The eyelid of albino rabbits (strain; Kbs: JW, KITAYAMA LABES CO., LTD.) were gently pulled apart from the eyeball, and 30 μL of each of Example 2, Comparative Example A, and Comparative Example B was added dropwise onto the cornea. After that, both the upper and lower eyelids were closed for 30 seconds. Thirty minutes after the installation, the ocular surface was washed well with 100 μL of saline, and then the lavage fluid was collected for each sample. At the same time, the lavage fluid for the ocular surface under forced blinking after installation was collected in the following procedures. The eyelid was gently pulled apart from the eyeball, and 30 μL was added dropwise onto the cornea. After that, both the upper and lower eyelids were closed for 30 seconds with a frequency of forced blinking once every 10 seconds. Thirty minutes after the installation, the ocular surface was washed well with 100 μL of saline, and then the lavage fluid was collected for sample.

Measurement was carried out on each sample for 480 nm (excitation wavelength) and 520 nm (absorption wavelength) to calculate the fluorescent dye concentration.

Figure 11:
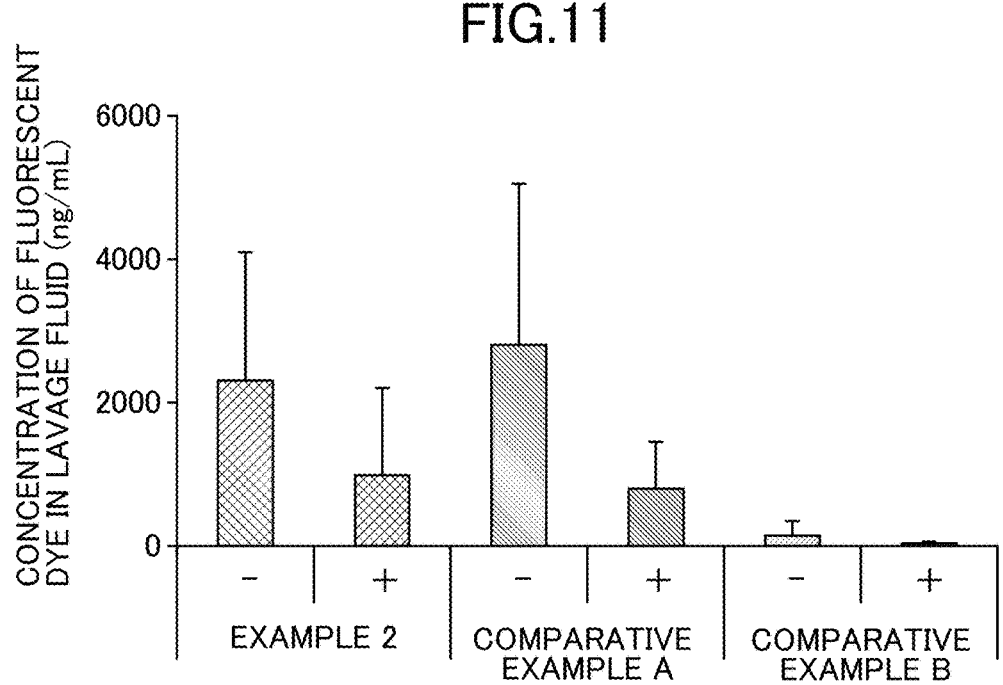
FIG. 11 is a graph showing results of evaluating ocular surface retention in Examples and Comparative Examples of the present invention.

FIG. 11 shows the results.

When the fluorescent dye concentrations in the lavage fluids for ocular surface were compared, Example 2 of the present invention exhibited the same fluorescent dye concentration as that of Comparative Example A and exhibited a fluorescent dye concentration higher than that of Comparative Example B regardless of blinking.

The results of Test Example 7 suggest that the compositions of the present invention are better than formulations of aqueous solution in terms of retention on the ocular surface.

TEST EXAMPLE 8

Measurement of Amount of Lacrima (1) Sample Solution

As an example, Example 2 of Table 1 was prepared in the same manner as Test Example 1, and an installation bottle was filled. Phosphate-buffered saline (GIBCO (registered trademark) PBS buffers, Life Technologies Corporation) was used for comparison.

A predetermined amount of benzalkonium chloride [number of carbon atoms in alkyl group: 14] (benzyldimethyl-tetradecylammonium chloride hydrate, Tokyo Chemical Industry Co., Ltd.) was dissolved in a trace amount of ethanol and was supplied with saline to a desired volume. Thus, a 0.1 (w/v)% BAC solution was prepared.

(2) Testing Method

Both eyes of albino rabbits (strain; Kbs: JW, KITAYAMA LABES CO., LTD.) were each instilled with 20 μL of 0.1 (w/v)% BAC solution using a micropipette twice a day (morning and evening) for 2 weeks every day.

The installation timing was shifted from the above such that both eyes were each instilled with 30 μL of Example 2 or phosphate-buffered saline three times a day at intervals of 3 hours between the morning and the evening for 2 weeks every day. Example 2 was instilled with an installation bottle. Phosphate-buffered saline was instilled with a micropipette. Lacrima was collected using a Schirmer test strip (AYUMI Pharmaceutical Corporation) before the start of testing and 1 week and 2 weeks after the start of testing.

Figure 12:
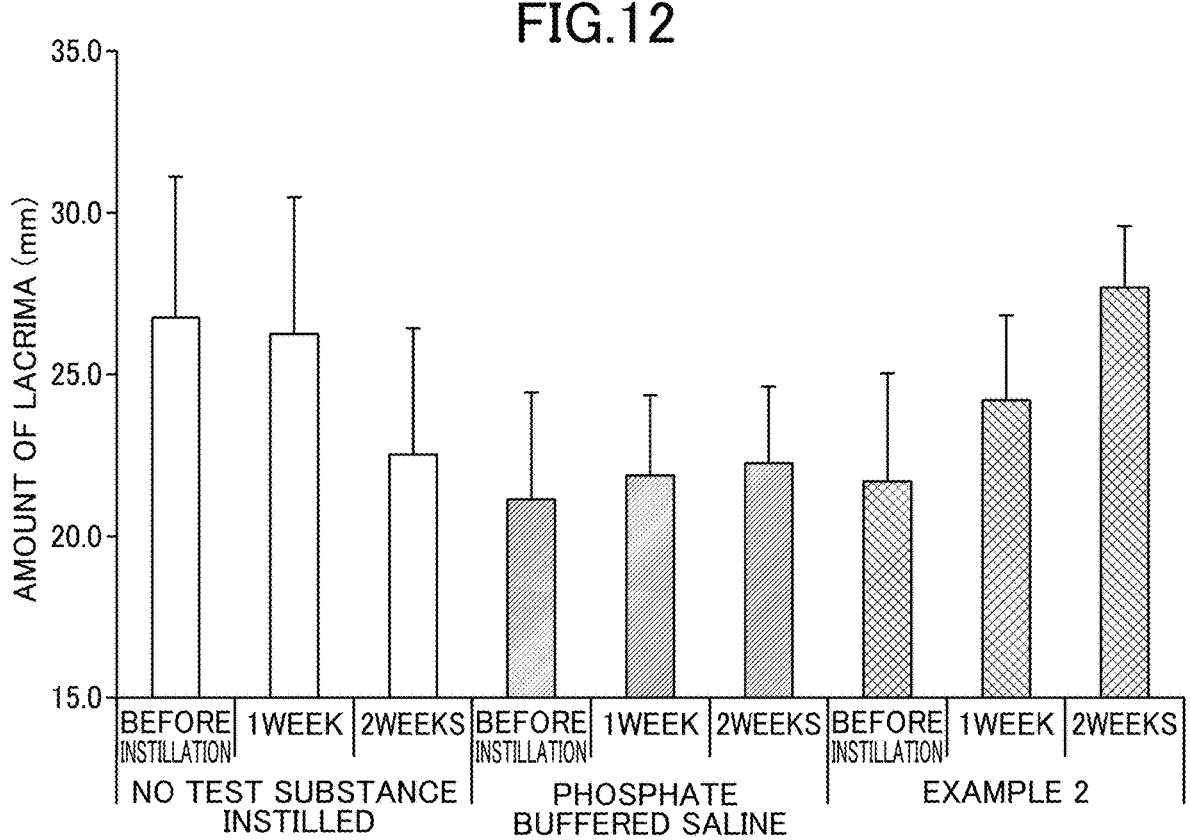
FIG. 12 is a graph showing results of measuring the amount of lacrima in Examples and Comparative Examples of the present invention.

FIG. 12 and Table 10 show the results.

TABLE 10

| | Amount of Lacrima (mm)* | |
|---|---|---|
| Administration Group | One Week | Two Weeks |
| No Test Substance Instilled | −0.5 ± 2.8 | −4.2 ± 4.0 |
| Phosphate-Buffered Saline | −0.8 ± 3.5 | 0.4 ± 2.7 |
| Example 2 | 2.5 ± 4.6 | 3.5 ± 2.2 |

*Average value ± standard deviation

Two weeks later, it was observed that the amount of lacrima decreased for the group not instilled with test substance, which was not instilled with either of Examples and comparative ones.

Two weeks later, it was observed that the amount of lacrima slightly increased for the group instilled with phosphate-buffered saline.

On the other hand, it was observed that the amount of lacrima increased over time for the group instilled with Example 2 of the present invention.

The results of Test Example 8 reveal that everyday installation of Example 2 suppresses the decrease in the amount of lacrima attributed to the installation of BAC aqueous solution and further increases the amount of lacrima.

TEST EXAMPLE 9

Effects on Corneal Damage (1) Sample Solution

As an example, Example 3 of Table 9 was prepared in the same manner as Test Example 1.

Saline (Otsuka Normal Saline (500 mL) (registered trademark), Otsuka Pharmaceutical Co., Ltd.) was used for comparison.

As a comparative example, SYSTANE (registered trademark) ULTRA manufactured by Novartis Pharma K.K. was designated as Comparative Example A.

After a predetermined amount of benzalkonium chloride (Tokyo Chemical Industry Co., Ltd.) was dissolved into a trace amount of ethanol, saline was supplied to obtain a desired volume. Thus, a 0.1 (w/v)% BAC solution was prepared.

(2) Testing Method

The present testing method referred to the method by Yuqiu Zhang et al. (Drug and chemical toxicology 2016.39 (4) 455-460).

Both eyes of albino rabbits (strain; Kbs: JW, KITAYAMA LABES CO., LTD.) were each instilled with 20 μL of 0.1 (w/v)% BAC solution using a micropipette three times a day (every 4 hours from the morning to the evening) every day. The instillation period was 42 days including the instillation day. Before instillation and after the 42-day instillation, the degree of disorder of the surface of the cornea was observed using a portable slit lamp Kowa SL-17 (manufactured by Kowa Company, Ltd., hereinafter referred to as SL-17).

Figure 13:
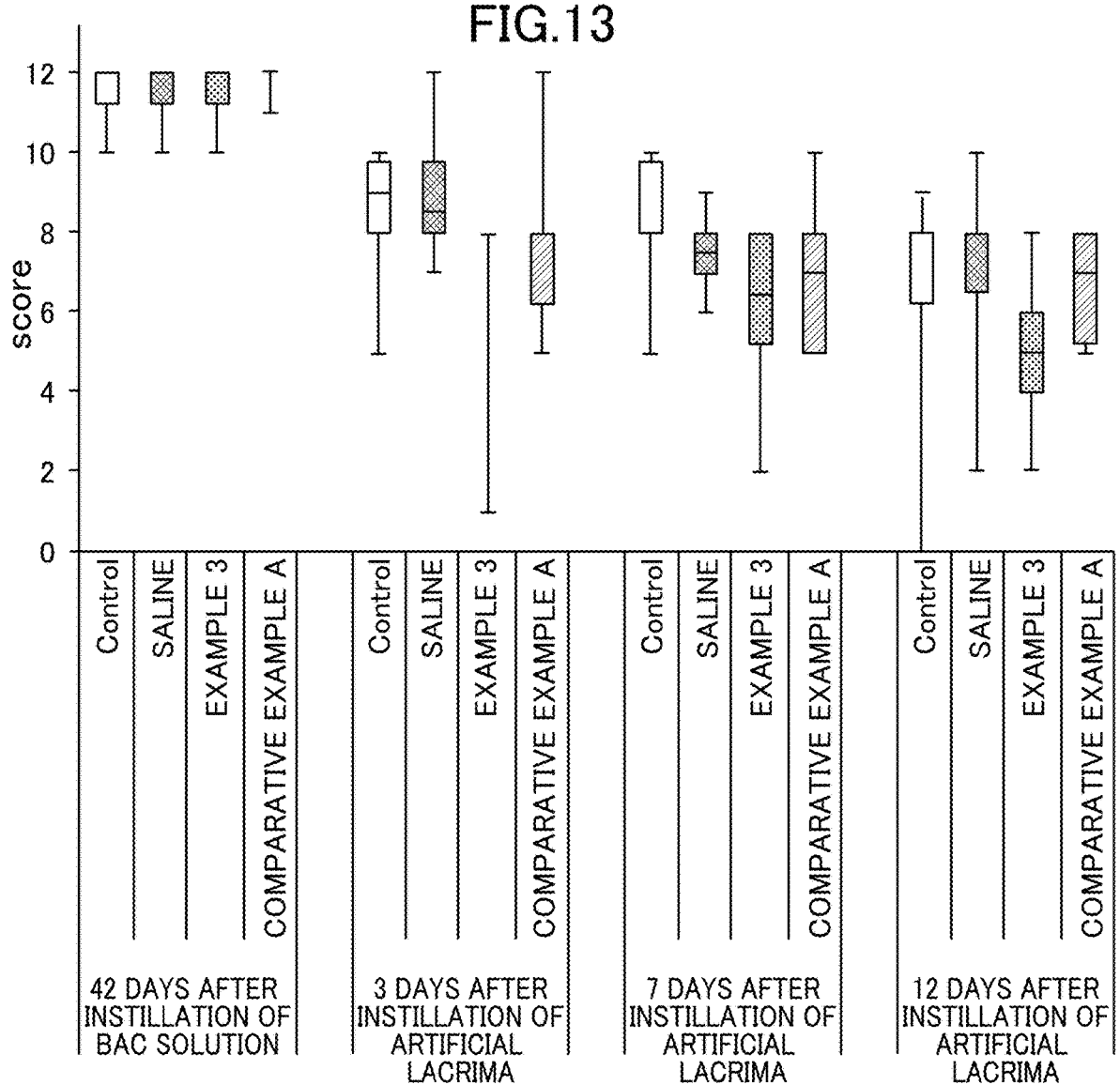
FIG. 13 is a graph showing results of evaluating recovery action from corneal disorder in Examples and Comparative Examples of the present invention.
Figure 14:
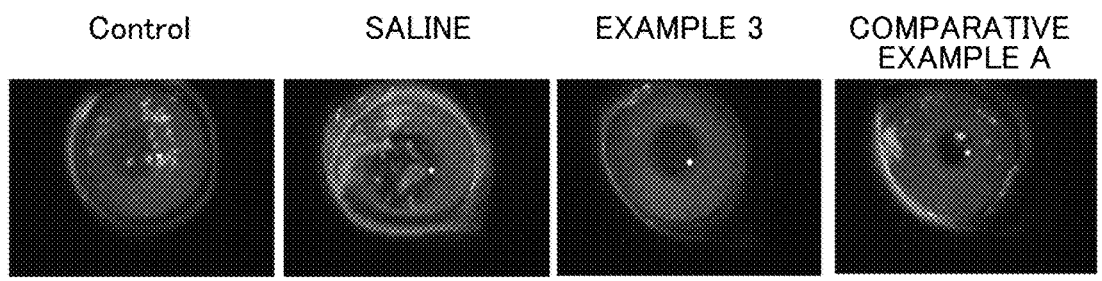
FIG. 14 is a photo of corneal disorder observed 12 days after the start of application in Examples and Comparative Examples of the present invention.

After the 42-day instillation of 0.1 (w/v)% BAC solution, both eyes of albino rabbits (five rabbits for each group, n=10 eyes) were each instilled with 30 μL of Example 3, Comparative Example A, and saline using a micropipette four times a day (every 2.5 to 3 hours from the morning to the evening) every day. The instillation period was 12 days including the instillation day. The cornea was stained with fluorescein and, after 3 minutes, was washed with saline. The SL-17 was used to observe the degree of disorder of the surface of the cornea. A corneal damage score was calculated for each group. FIG. 13 and FIG. 14 show the results. FIG. 14 shows photos of the corneal disorder 12 days after the start of instillation of no treatment (Control), saline, Example 3, and Comparative Example A.

By repeatedly instilling the 0.1% BAC solution, a serious conical disorder was confirmed. After the end of instillation of the BAC solution, it was shown that the corneal disorder slowly recovered in the no treatment (Control) group and in the group instilled with saline. In addition, it was shown that the degree of recovery from the corneal disorder was better for the group instilled with Comparative Example A than the no treatment group and the group instilled with saline. Moreover, in the group instilled with Example 3 of the present invention, it was shown that recovery from the corneal disorder was better than any other group.

The results of Test Example 9 suggest that the corneal disorder is recovered early by repeatedly instilling Example 3.

INDUSTRIAL APPLICABILITY

An ophthalmic aqueous composition of the present invention, which suddenly increases viscosity at temperatures around the body temperature, can retain the lacrima on the ocular surface if administer into an organism because it rapidly gelates and remains at the site of administration. In addition, if the composition increases viscosity at a temperature of 30° C. or more in a certain region, season, and the like, the composition easily changes into a composition having a high fluidity simply by applying a weak force thereto. Thus, storage at cool place is unnecessary and the composition is portable.

The invention claimed is:

1. An ophthalmic aqueous composition comprising:
   (A) methyl cellulose having a label viscosity of 4 and methyl cellulose having a label viscosity of 15 in a total amount having a mass ratio of 1:4 to 4:1 and combined total concentration of 0.2 to 5 w/v %;
   (B) polyethylene glycol having a weight average molecular weight of 4000 or 8000 at 0.5 to 4.0 w/v %;
   (C) polyvinylpyrrolidone K25 at 0.5 to 4.0 w/v %; and
   (D) citric acid or sodium salts thereof at 1.0 to 4.0 w/v %,
   wherein all w/v % are based on the total amount of the composition, and
   wherein the ophthalmic aqueous composition has a gelling property.

2. A method for protecting cornea, mitigating a corneal epithelial disorder, or recovery from a corneal disorder, comprising administrating to a subject in need thereof a composition which comprises:
   (A) methyl cellulose having a label viscosity of 4 and methyl cellulose having a label viscosity of 15 in a total amount having a mass ratio of 1:4 to 4:1 and a combined total concentration of 0.2 to 5 w/v %;
   (B) polyethylene glycol having a weight average molecular weight of 4000 or 8000 at 0.5 to 4.0 w/v %;
   (C) polyvinylpyrrolidone K25 at 0.5 to 4.0 w/v %; and
   (D) citric acid or sodium salts thereof at 1.0 to 4.0 w/v %,
   wherein all w/v % are based on the total amount of the composition, and
   wherein the ophthalmic aqueous composition has a gelling property.

* * * * *